(12) United States Patent
Wang et al.

(10) Patent No.: US 11,337,663 B2
(45) Date of Patent: May 24, 2022

(54) RAPID FILTRATION METHODS FOR DUAL-ENERGY X-RAY CT

(71) Applicant: RENSSELAER POLYTECHNIC INSTITUTE, Troy, NY (US)

(72) Inventors: Ge Wang, Loudonville, NY (US); Wenxiang Cong, Albany, NY (US); Yan Xi, Syracuse, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 102 days.

(21) Appl. No.: 16/092,393

(22) PCT Filed: Apr. 6, 2017

(86) PCT No.: PCT/US2017/026322
§ 371 (c)(1),
(2) Date: Oct. 9, 2018

(87) PCT Pub. No.: WO2017/176976
PCT Pub. Date: Oct. 12, 2017

(65) Prior Publication Data
US 2021/0212643 A1    Jul. 15, 2021

Related U.S. Application Data

(60) Provisional application No. 62/319,881, filed on Apr. 8, 2016, provisional application No. 62/333,882, filed on May 10, 2016.

(51) Int. Cl.
*A61B 6/00* (2006.01)
*A61B 6/03* (2006.01)

(52) U.S. Cl.
CPC .......... *A61B 6/4042* (2013.01); *A61B 6/032* (2013.01); *A61B 6/405* (2013.01); *A61B 6/482* (2013.01)

(58) Field of Classification Search
CPC ....... A61B 6/032; A61B 6/4035; A61B 6/482; A61B 6/4007; A61B 6/4085;
(Continued)

(56) References Cited

U.S. PATENT DOCUMENTS

2011/0261924 A1    10/2011  Bredno
2012/0281811 A1*   11/2012  Kohara .................... A61B 6/06
                                                    378/62
(Continued)

FOREIGN PATENT DOCUMENTS

WO        2016038504 A1    3/2016

OTHER PUBLICATIONS

International search report for PCT/US2017/026322 dated Jun. 19, 2017.

*Primary Examiner* — Irakli Kiknadze
(74) *Attorney, Agent, or Firm* — Murtha Cullina LLP; Anthony P. Gangemi

(57) ABSTRACT

Systems and method for performing X-ray computed tomography (CT) that can improve spectral separation and decrease motion artifacts without increasing radiation dose are provided. The systems and method can be used with either a kVp-switching source or a single-kVp source. When used with a kVp-switching source, an absorption grating and a filter grating can be disposed between the X-ray source and the sample to be imaged. Relative motion of the filter and absorption gratings can by synchronized to the kVp switching frequency of the X-ray source. When used with a single-kVp source, a combination of absorption and filter gratings can be used and can be driven in an oscillation movement that is optimized for a single-kVp X-ray source. With a single-kVp source, the absorption grating can also be omitted and the filter grating can remain stationary.

11 Claims, 13 Drawing Sheets

FIG. 2

(58) Field of Classification Search
CPC ..... A61B 6/5258; A61B 6/4042; A61B 6/405; A61B 6/5205; A61B 6/037; A61B 6/4417; A61B 6/025; A61B 6/035; A61B 6/0492; A61B 6/4208; A61B 6/4258; A61B 6/4435; A61B 6/00; A61B 6/4291; A61B 6/484; A61B 6/4441; A61B 6/582; A61B 6/583; A61B 6/107; A61B 6/481; A61B 6/502; A61B 6/504; A61B 6/5211; A61B 6/5235; A61B 6/5282; A61B 6/4452; A61B 6/4021; A61B 6/4233; G01N 2223/303; G01N 2223/6126; G01N 23/041; G01N 23/044; G01N 23/046; G01N 23/20075; G01N 23/04; G02B 5/1838; G21K 1/06; G21K 1/10; G21K 2207/005; G21K 1/067; G21K 2201/067; G21K 7/00; G01V 8/005; H01H 1/06; H01H 3/16; H01M 10/0525; H01M 4/366; H01M 4/525; H01M 4/5825; H01J 2235/00
USPC ................................ 378/4–19, 36, 62, 85–87
See application file for complete search history.

(56) References Cited

U.S. PATENT DOCUMENTS

| | | |
|---|---|---|
| 2013/0266115 A1 | 10/2013 | Fan et al. |
| 2014/0037059 A1 | 2/2014 | Suft |
| 2014/0185746 A1 | 7/2014 | Baturin et al. |
| 2014/0226783 A1* | 8/2014 | Ning ...................... A61B 6/502 378/5 |
| 2017/0273642 A1* | 9/2017 | Engel ....................... G21K 1/10 |

\* cited by examiner (a)

(b)    (c)    (d)

RAPID FILTRATION METHODS FOR DUAL-ENERGY X-RAY CT

CROSS REFERENCE TO RELATED APPLICATIONS

This application claims the benefit of U.S. Provisional Patent Application Ser. No. 62/319,881, filed Apr. 8, 2016, and U.S. Provisional Patent Application Ser. No. 62/333,882, filed May 10, 2016, the disclosures of which are hereby incorporated by reference in their entirety, including any figures, tables, and drawings.

BACKGROUND

Since the invention of X-ray computed tomography (CT) in 1971, it has gone through many improvements, including fanbeam, multi-slice and cone-beam spiral CT methods, which add longitudinal dimension to CT images. Also, dual-energy/multi-energy CT technologies add spectral dimension to CT images. Even though dual-energy CT has some advantages, monochromatic imaging and material decomposition can be performed, which reduces X-ray radiation dose and facilitates a number of important applications. Multi-energy CT is an emerging field, but it still needs time to become mature and enter the clinical world.

Currently, dual-energy CT technologies can be classified into three categories: kVp-switching; dual-layer detection; and dual-source scanning. The kVp-switching method is an X-ray source technology in which low- and high-energy X-ray beams are alternatingly emitted during a scan. The dual-layer detector method is based on a detector innovation so that low- and high-energy data are collected in two sensor layers respectively. These two methods both use a single X-ray source to generate dual-energy datasets. Thus, the resultant low- and high-energy datasets share the same X-ray filter placed in front of the X-ray source. Different from the single-source-based dual-energy CT systems, a dual-source system includes two imaging subsystems. The dual-source CT system is more expensive, and there is a temporal discrepancy between low- and high-energy data acquisitions. Breathing, heart beating, and patient motion causes artifacts in reconstructed images, compromising material decomposition and monochromatic imaging.

BRIEF SUMMARY

Embodiments of the subject invention include systems and method for performing X-ray computed tomography (CT) that can improve spectral separation and decrease motion artifacts without increasing radiation dose to which a patient is exposed during imaging. Systems and methods of embodiments of the subject invention can be used with either a kVp-switching source or a single-kVp source. When used with a kVp-switching source, an absorption grating and a filter grating can be disposed between the X-ray source and where a sample/patient to be imaged would be (or is) located (e.g., in front of the X-ray source). Relative motion of the filter and absorption gratings can by synchronized to the kVp switching frequency of the X-ray source. Different filter regions can be exposed to X-rays at various time instants, thereby producing low- and high-energy X-rays accordingly. When used with a single-kVp source, a combination of absorption and filter gratings can be used and can be driven in an oscillation movement that is optimized for a single-kVp X-ray source. In certain embodiments, only a filter grating alone is required, and the filter grating can be stationary with respect to the X-ray source. In a specific embodiment, the filter grating can be just a two-strip filter.

In an embodiment, a system for performing X-ray CT imaging can comprise: an X-ray source; a detector for detecting X-ray radiation from the source; a filter grating disposed between the source and the detector; and an absorption grating disposed between the filter grating and the source. At least one of the absorption grating and the filter grating can be configured to move relative to the other during operation of the source. The filter grating can be positioned closer to the source than it is to the detector (for example, in front of the source). The source can be either a kVp-switching source or a non-kVp-switching source, and the oscillation (relative movement) between the gratings can be optimized depending on what type of source is used.

In another embodiment, a system for performing X-ray CT imaging can comprise: a single-kVp X-ray source (non-kVp-switching X-ray source); a detector for detecting X-ray radiation from the source; and a filter grating disposed between the source and the detector. The filter grating can be positioned closer to the source than it is to the detector (for example, in front of the source, and the system can specifically exclude an absorption grating. The filter grating can be configured to be stationary during operation of the source. Image reconstruction for such a system can be based on a non-linear X-ray data generation model. The image reconstruction can include non-linear data modeling and compressed sensing.

DETAILED DESCRIPTION

Embodiments of the subject invention include systems and method for performing X-ray computed tomography (CT) that can improve spectral separation and decrease motion artifacts without increasing radiation dose to which a patient (e.g., a mammal patient such as a human) or sample is exposed during imaging. Systems and methods of embodiments of the subject invention can be used with either a kVp-switching (kilovolt-peak-switching (voltage-alternating)) X-ray source or a single-kVp (non-kVp-switching) X-ray source (e.g., X-ray tube). When used with a kVp-switching X-ray source, an absorption grating and a filter grating can be disposed between the X-ray source and where a sample/patient to be imaged would be (or is) located (e.g., in front of the X-ray source). Relative motion of the filter and absorption gratings can by synchronized to the kVp switching frequency of the X-ray source (e.g., X-ray tube). Different filter regions can be exposed to X-rays at various time instants, thereby producing low- and high-energy X-rays accordingly. When used with a single-kVp (non-kVp-switching) X-ray source, a combination of absorption and filter gratings can be used and can be driven in an oscillation movement (relative to each other) that is optimized for a single-kVp X-ray source. With X-rays of the same energy spectrum, different filtration materials can be used to generate X-rays in two (or more) energy spectra (one of them at any given time instant). In certain embodiments, only a filter grating alone is required, and the filter grating can be stationary with respect to the X-ray source (e.g., X-ray tube). This stationary approach presents a minimum demand for CT hardware enhancement. In a specific embodiment, the filter grating can be just a two-strip filter.

Figure 1:
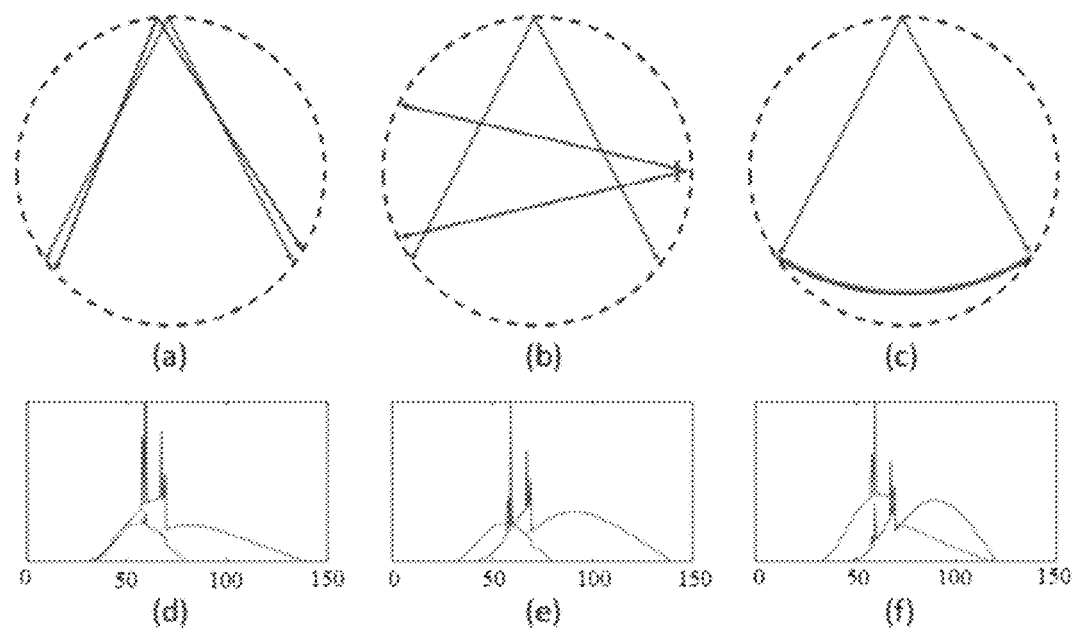
FIG. 1A shows a depiction of kVp-switching X-ray computed tomography (CT).
FIG. 1B shows a depiction of dual-layer detection X-ray CT.
FIG. 1C shows a depiction of dual-source scanning X-ray CT.
FIG. 1D shows a plot of low- and high-energy spectra for kVp-switching X-ray CT.
FIG. 1E shows a plot of low- and high-energy spectra for dual-layer detection X-ray CT.
FIG. 1F shows a plot of low- and high-energy spectra for dual-source scanning X-ray CT.

Dual-energy CT technologies can be classified into the three categories: kVp-switching; dual-layer detection; and dual-source scanning. FIGS. 1A-1C are depictions of beams for kVp-switching, dual-layer detection, and dual-source scanning, respectively. The kVp-switching method is an X-ray source technology in which low- and high-energy x-ray beams are alternatingly emitted during a scan. The dual-layer detector method is based on a detector innovation so that low- and high-energy data are collected in two sensor layers respectively. These two methods both use a single X-ray source to generate dual-energy datasets. Generally, the resultant low- and high-energy datasets share the same X-ray filter placed in front of the X-ray source, and as a result, the low- and high-energy X-rays are not well separated, as shown in FIGS. 1D and 1E, which are plots for conventional kVp-switching and dual-layer detection, respectively, of low- and high-energy spectra. In a dual-source system, there are two imaging subsystems. Because the X-ray sources are independent, different X-ray filters can be customized for more flexible X-ray filtration, and the low- and high energy X-ray entrance spectra can be individually shaped, yielding a better spectral separation, as shown in FIG. 1F. However, dual-source CT systems are more expensive and result in a temporal discrepancy between low- and high-energy data acquisitions. Breathing, heart beating, and patient motion cause artifacts in reconstructed images for related art dual-source systems, compromising material decomposition and monochromatic imaging.

Embodiments of the subject invention can simultaneously address the spectral overlapping problem with kVp-switching and dual-layer detection systems, as well as the motion artifact problem with a dual-source scanner. Grating oriented line-wise filtration (GOLF) systems and methods can enable interlaced filtration patterns for superior energy separation. An X-ray filtration device can be easily integrated into a CT scanner and its scanning procedure. Depending on the X-ray source type, three main filtration systems/methods can be used, which can be referred to as $GOLF_k$, $GOLF_c$, and $GOLF_s$.

$GOLF_k$ can be used for a kVp-switching X-ray source. $GOLF_k$ can combine an absorption grating and a filter grating disposed between the X-ray source and where a sample/patient to be imaged would be (or is) located (e.g., in front of the X-ray source). $GOLF_k$ can synchronize relative motion of the filter and absorption gratings to the kVp switching frequency of the X-ray source (e.g., X-ray tube). For example, the filter grating can be driven by a high-precision manipulator, such as a piezo-electrical motor for rapid oscillation of one grating relative to the other. Different filter regions can be exposed to X-rays at various time instants, thereby producing low- and high-energy X-rays accordingly.

$GOLF_c$ and $GOLF_s$ can work with a conventional (e.g., non-kVp-switching) X-ray source. $GOLF_c$ can use a combination of absorption and filter gratings optimized for an X-ray source (e.g., X-ray tube) without kVp-switching. The X-ray filter grating and/or the X-ray absorption grating can be driven in an oscillation movement relative to each other. $GOLF_s$ only requires a filter grating alone that is stationary with respect to the X-ray source (e.g., X-ray tube). This stationary approach presents a minimum demand for CT hardware enhancement. In a specific embodiment of $GOLF_s$, the filter grating can be just a two-strip filter.

Figure 2:
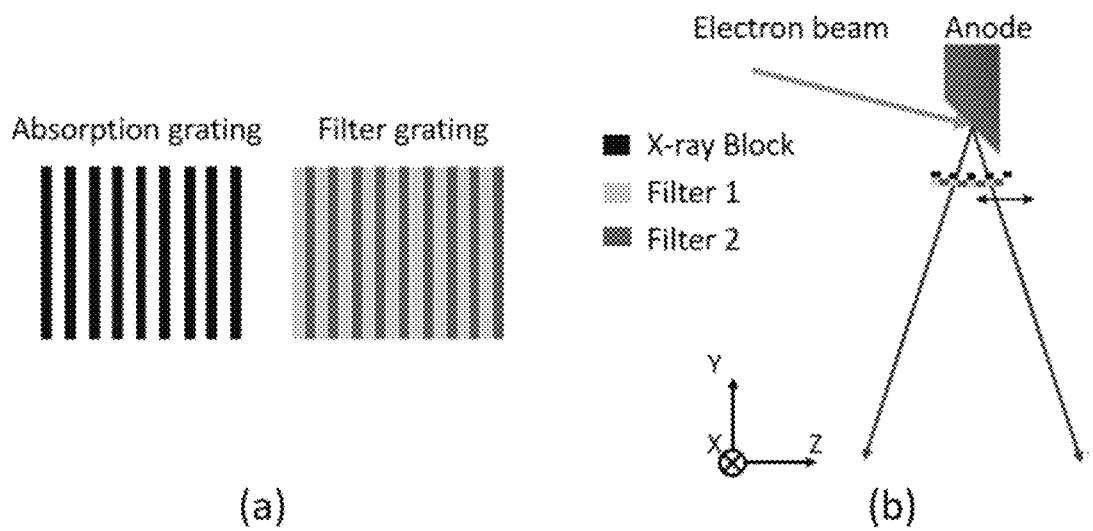
FIG. 2A shows example filter and absorption gratings that can be used in a system or method according to an embodiment of the subject invention.
FIG. 2B shows a layout of gratings disposed in front of an X-ray source according to an embodiment of the subject invention.
FIG. 2C shows a stationary curved absorption grating that can be used according to an embodiment of the subject invention.
FIG. 2D shows a top view of a grating having slits designed for a curved geometry according to an embodiment of the subject invention.
Figure 2:
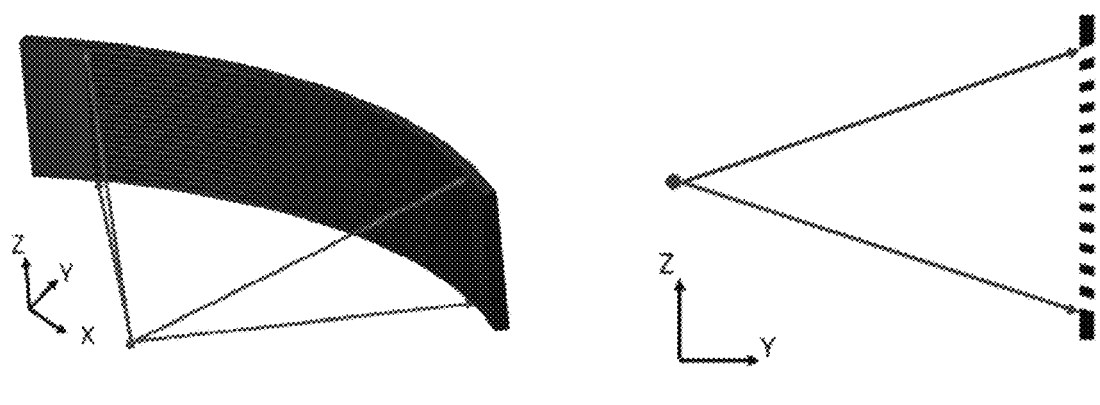

FIG. 2A shows example filter and absorption gratings that can be used in a GOLFk system or method according to an embodiment of the subject invention, and FIG. 2B shows a layout of gratings disposed in front of the X-ray source. Although FIG. 2A shows an X-ray tube with electron beam and anode as the X-ray source, along with two filters making up the filter grating, these are for exemplary purposes only and should not be construed as limiting. Referring to FIGS. 2A and 2B, the absorption grating can be disposed between the X-ray source and the filter grating, and the gratings can be moved relative to each other during operation of the X-ray source. The movement of the gratings can be in a direction parallel to the front face of the grating (i.e., in the z-direction as depicted in FIG. 2B). In addition, the filter grating can include one filter or a plurality of filters. The absorption grating can comprise or be entirely composed of an X-ray absorption material (e.g., gold) to let X-rays go through its open slits only. In this way, the X-rays allowed to go through can be controlled by choosing the width of each slit, the number of slits, the width between slits, and the number of solid portions (non-slits). The width of slits and/or solid portions can be uniform across the grating, individually or in total, or such widths can vary. The filter grating can spectrally modify the X-ray beam through grating materials. For example, the filter grating can include thin metal strips interlacing one or more filtering materials (e.g., two filtering materials). The duty cycle of the filter grating can be, for example, 50%, though embodiments are not limited thereto. Through relative displacement of the two gratings, incident X-rays are filtered at different time instants by different kinds of filtering strips. Also, in further embodiments, a plurality of absorption gratings and/or filter gratings can be used.

The two gratings can be overlaid in front of the X-ray source, as shown in FIG. 2B. In the kVp-switching based dual-energy CT system, the entrance X-rays can alternate at low- and high-energy levels. Synchronously, the filter grating can be driven at the same high-frequency relative to the absorption grating. For low-energy X-ray imaging, the filter grating can oscillate in such a way that the first set of filtering strips happen to be in the X-ray path. Then, for high-energy X-ray imaging, the second set of filtering strips can be exposed to the X-ray source.

In certain embodiments, the gratings can be configured to fit a curved geometry. FIG. 2C shows a stationary curved absorption grating, and FIG. 2D shows a top view of a grating having slits designed for a curved geometry. Referring to FIGS. 2C and 2D, one or more gratings can be configured to fit a curved geometry, such as for a third generation CT implementation. The strips in a curved absorption grating can be aligned according to X-ray emitting angles in a cone geometry, as shown in FIG. 2C. In a specific embodiment, the period of the filter grating can be 0.5 mm with a duty cycle of 50%, the strips in the flat absorption grating can be made of 1 mm gold strips with high X-ray absorption, and the materials of the filter grating are air and 1 mm tin corresponding to low- and high-energy X-ray filtrations, respectively.

In embodiments of a GOLFk system or method, the motion direction of the filter grating can be perpendicular to the longitudinal direction of the filter strips. Thus, half (or about half) of the original X-rays can be blocked by the absorption grating, and the other half (or about half) can get filtered by the corresponding strips of the filter grating. With kVp-switching based dual-energy CT, the low- and high-energy X-rays are emitted in turn.

In many embodiments of a GOLFk system or method, the filter grating vibration frequency can be matched to the X-ray kVp-switching frequency. Also, the vibration amplitude can be optimized according to the duty cycle of the absorption grating. With the duty cycle being ½r, the optimized vibration amplitude is $$(1-r)\frac{p}{2}.$$

Figure 3:
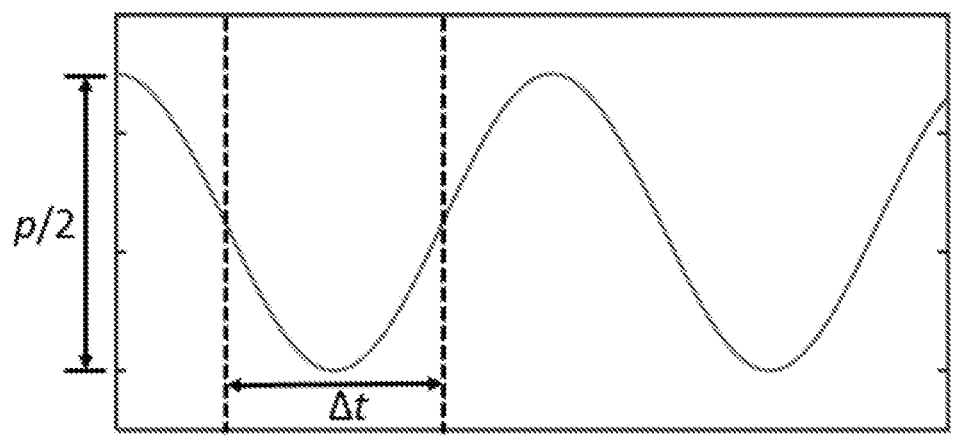
FIG. 3A shows an oscillation curve of a filter grating.
FIG. 3B shows a top view of an absorption grating (left) and a filter grating (right) including two different types of filter (different shadings) according to an embodiment of the subject invention.
FIG. 3C shows a top view of an absorption grating (left) and a filter grating (right) including two different types of filter (different shadings) according to an embodiment of the subject invention.
FIG. 3D shows a top view of an absorption grating (left) and a filter grating (right) including two different types of filter (different shadings) according to an embodiment of the subject invention.
Figure 3:
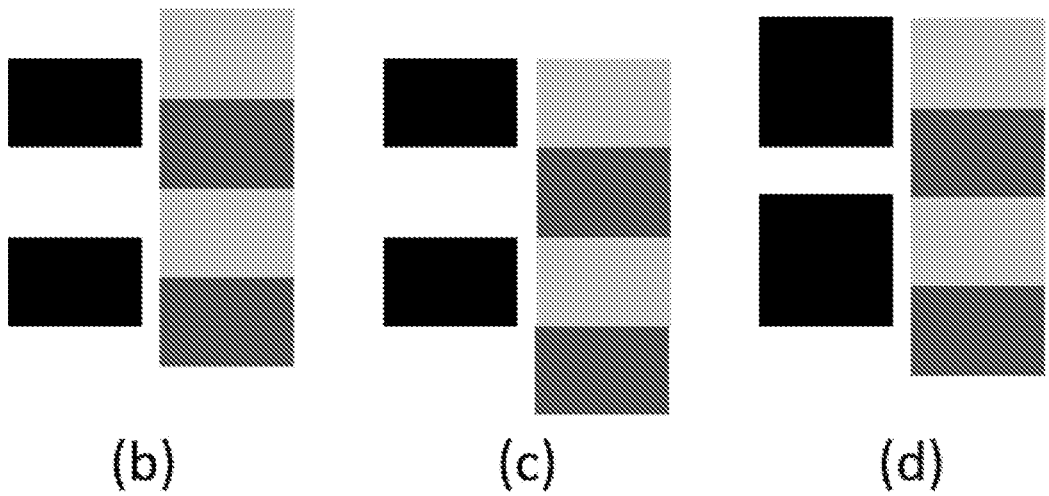

FIG. 3A snows an oscillation curve of a filter grating according to an embodiment. Referring to FIG. 3A, the oscillation period is equal to half the time interval between two adjacent X-ray projections in the kVp-switching CT scan. FIGS. 3B-3D show top views of an absorption grating (left) and a filter grating (right) including two different types of filter (different shadings). An ideal X-ray filtration setting is shown in FIG. 3C, in which the absorption grating and the filter grating are in a perfect alignment, without filter materials mixed in the x-ray beam. Referring to FIG. 3C, the filter grating can be aligned such that one of its filter materials matches up with each slit of the absorption grating. However, during the exposure period t, the absorption grating and the filter grating are in relative motion, and the X-rays are filtered by two filters with a changing material mixture, for example leading to the orientation shown in FIG. 3B at certain times. FIG. 3D shows an example absorption grating with a narrower grating opening. Referring to FIG. 3D, the configuration with a narrower opening minimizes the problems that may be caused by mixed filtration, but this can come at a cost of reduced photon efficiency.

Figure 4:
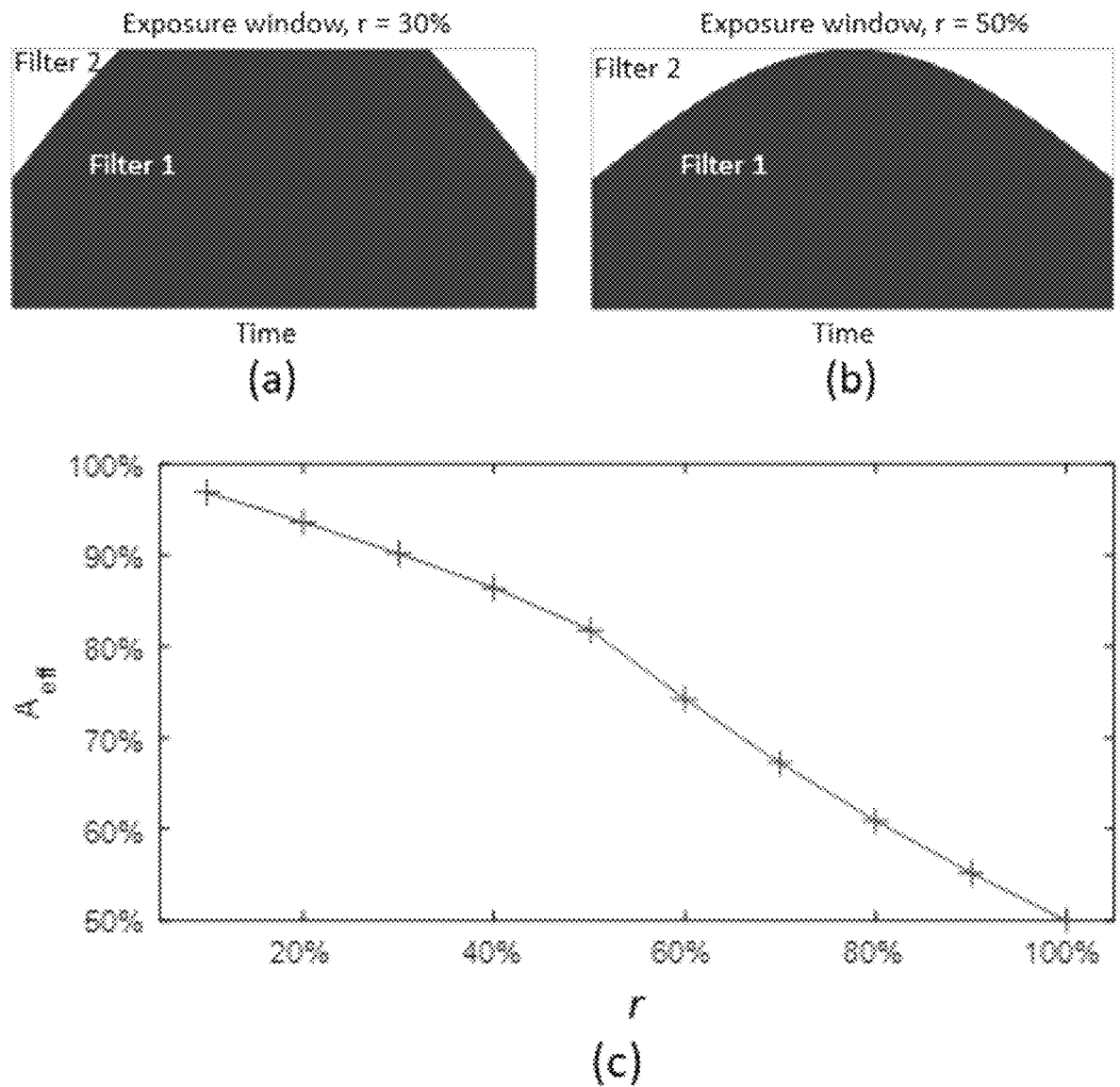
FIG. 4A shows the exposure window for two different types of filters of the same filter grating at a duty cycle of 30%, with the vibration amplitude being half of the filter grating period, according to an embodiment of the subject invention.
FIG. 4B shows the exposure window for two different types of filters of the same filter grating at a duty cycle of 50%, with the vibration amplitude being half of the filter grating period, according to an embodiment of the subject invention.
FIG. 4C shows a plot of effective filtration area as a function of absorption grating duty cycle (r).

FIGS. 4A-4B show the exposure window for two different types of filters of the same filter grating at duty cycles of 30% and 50%, respectively, for the vibration amplitude being half of the filter grating period. FIG. 4C shows a plot of effective filtration area as a function of absorption grating duty cycle (r). FIGS. 4A-4C are all for a $GOLF_k$ system/method according to an embodiment of the subject invention. Referring to FIGS. 4A and 4B, within the exposure window Δt, Filters 1 and 2 are gradually exposed through the absorption grating opening, in which Filter 1 offers the correct filtration, while Filter 2 introduces a contamination. Referring to FIG. 4C, by increasing the open ratio to 1, the filtration method is degraded to the conventional kVp-switching method.

Figure 5:
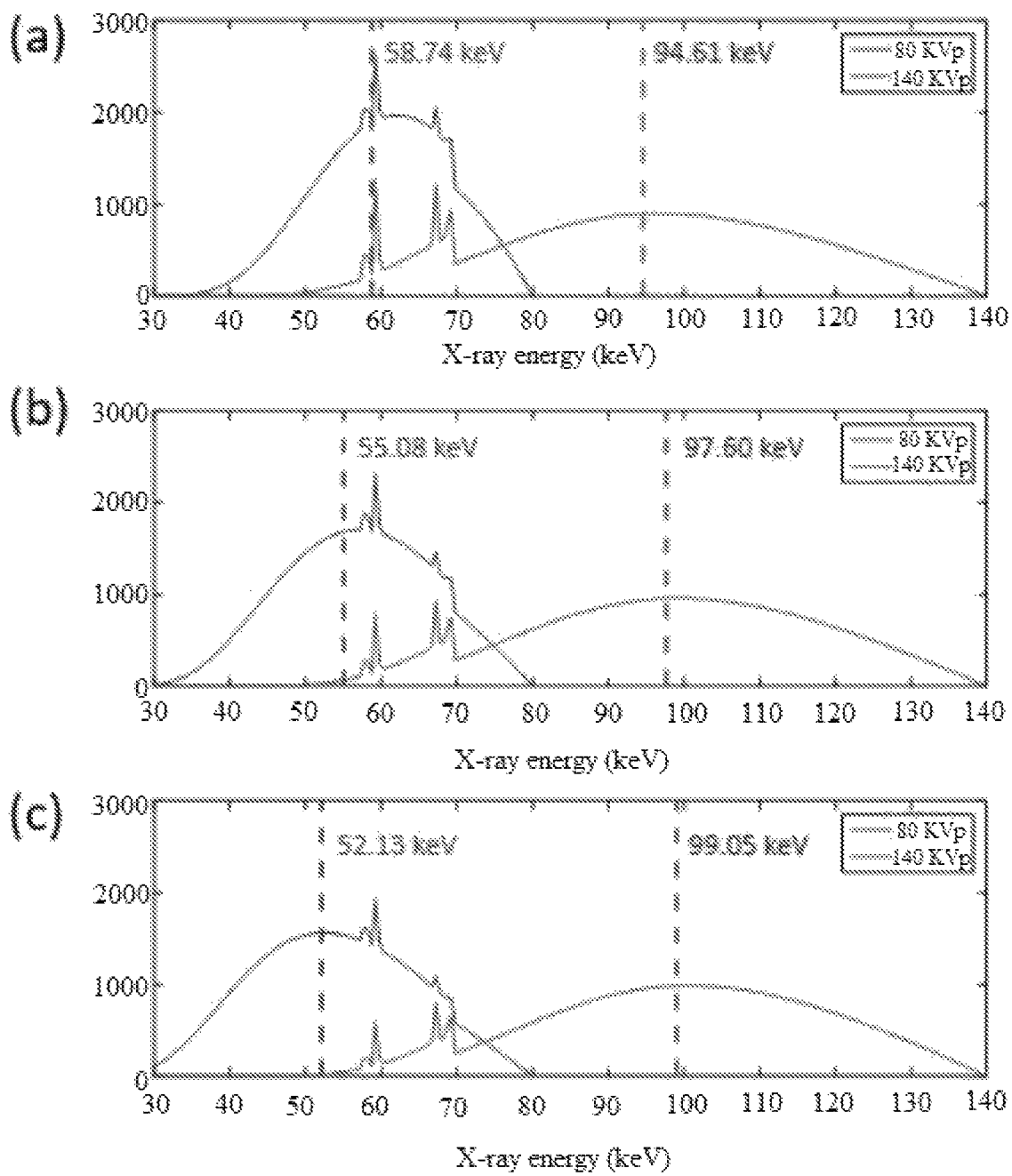
FIG. 5A shows a plot of spectral distributions at an absorption grating duty cycles of 70%.
FIG. 5B shows a plot of spectral distributions at an absorption grating duty cycles of 50%.
FIG. 5C shows a plot of spectral distributions at an absorption grating duty cycles of 30%.

FIGS. 5A-5C show plots of spectral distributions for a $GOLF_k$ system/method according to an embodiment of the subject invention, at absorption grating duty cycles of 70%, 50%, and 30%, respectively. In FIGS. 5A-5C, vertical dotted lines indicate corresponding mean energies (also labeled on the plots), and in each of these plots, the left-most plotted line is for an energy of 80 kVp and the right-most plotted line is for an energy of 140 kVp. The plots in FIGS. 5A-5C assume air and 1 mm tin as two filtering materials in the filter grating. Referring to FIGS. 5A-5C, a narrower absorption grating opening results in better separation of the spectra; though, a narrow absorption grating opening can decrease the X-ray efficiency.

Figure 6:
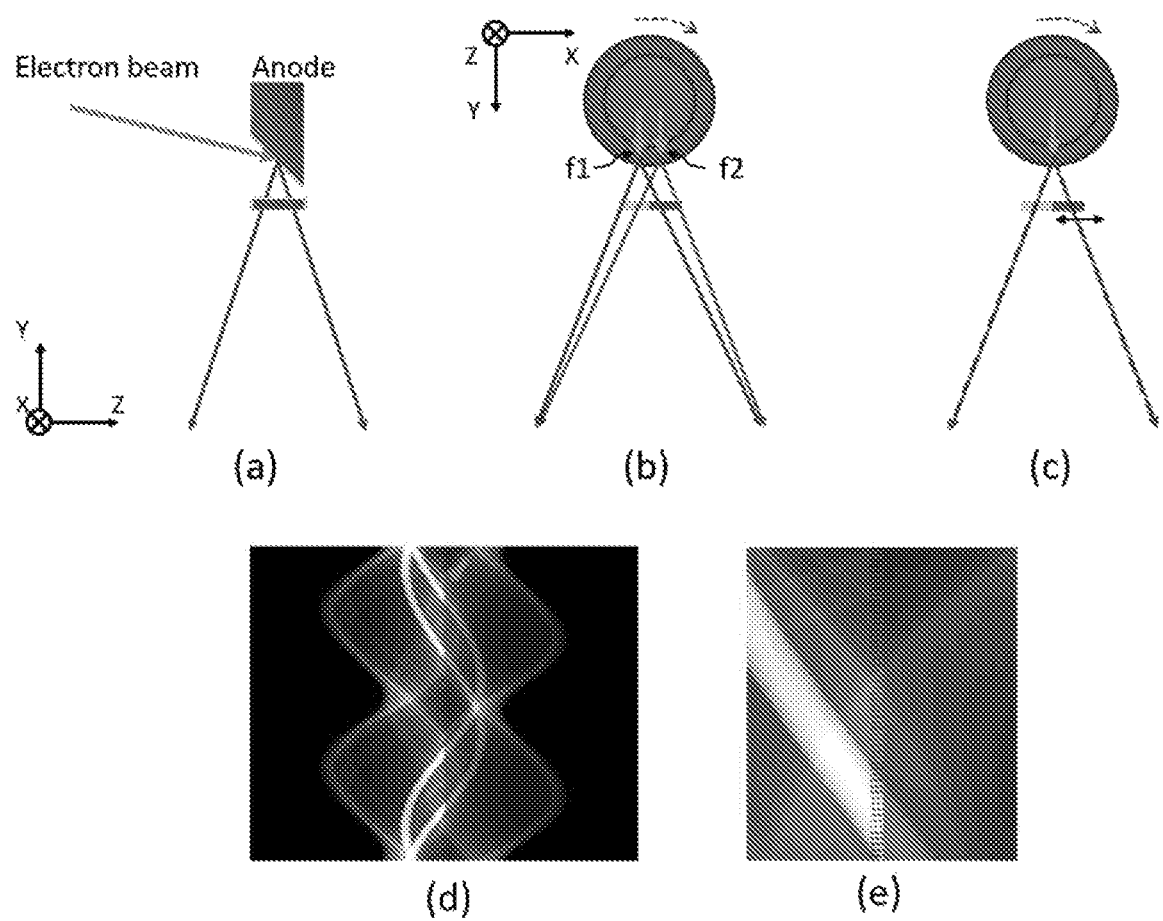
FIG. 6A shows a top schematic view of a setup according to an embodiment of the subject invention.
FIG. 6B shows a top schematic view of a setup according to an embodiment of the subject invention.
FIG. 6C shows a top schematic view of a setup according to an embodiment of the subject invention.
FIG. 6D shows a collected CT sinogram.
FIG. 6E shows an image of collected data for a CT scan.

$GOLF_c$ and $GOLF_s$ systems and methods as described herein can be used with an X-ray source with no kVp-switching (and, optionally, without any other advanced features). FIGS. 6A-6C show top schematic views of a $GOLF_c$ setup according to various embodiments of the subject invention. The X-ray sources shown in FIGS. 6A-6C are for exemplary purposes only and should not be construed as limiting. In an embodiment, a degraded grating filter can include only two filter strips, one of which is low-absorption material (e.g., air or aluminum) and the other is a high-absorption material (e.g., tin). The low-absorption material can keep the original X-ray beam while the high-absorption material can harden the X-ray beam (see also FIGS. 6A-6C). With this $GOLF_c$ setup, two mean-energy parts can be formed in one full X-ray beam. FIG. 6D shows the collected CT sinogram, in which the left side is low mean-energy data, and the other side high mean-energy data, which are for low-energy and high-energy image reconstruction, respectively. Given the size of the X-ray focal spot, a penumbra can be seen along the middle line of the sinogram, as marked by the (red) arrow in FIG. 6D, which will influence the image reconstruction. To address this effect, relative displacement between the X-ray focal spot and filter grating can be introduced. It can be implemented, for example, via e-beam control in the X-ray tube (the flying focal spot method) or filter oscillation outside the X-ray source; these two methods are equivalent in principle.

In a specific embodiment of $GOLF_c$, the low- and high-absorption materials can be 0.1-mm and 1.0-mm tin materials, respectively, and the size of the X-ray focal spot can be 1 mm. In this case, the penumbra in the detector plane is about 8 mm in width under the imaging geometry of a system in which the filter is 10 cm away from the X-ray focal spot. By controlling the X-ray focal spot flying in 1 mm along the X-axis or oscillating the filter with 1 mm peak shift, the collected data are shown in FIG. 6E, which can remove the penumbra effect although the amount of effective central data are reduced by half. As a result, the middle strip in FIG. 6D can become usable after longitudinal data interpolation for dual-energy image reconstruction via filtered back projection (see, e.g., references [20] and [21] in the References section, both of which are hereby incorporated herein by reference in their entireties).

Figure 7:
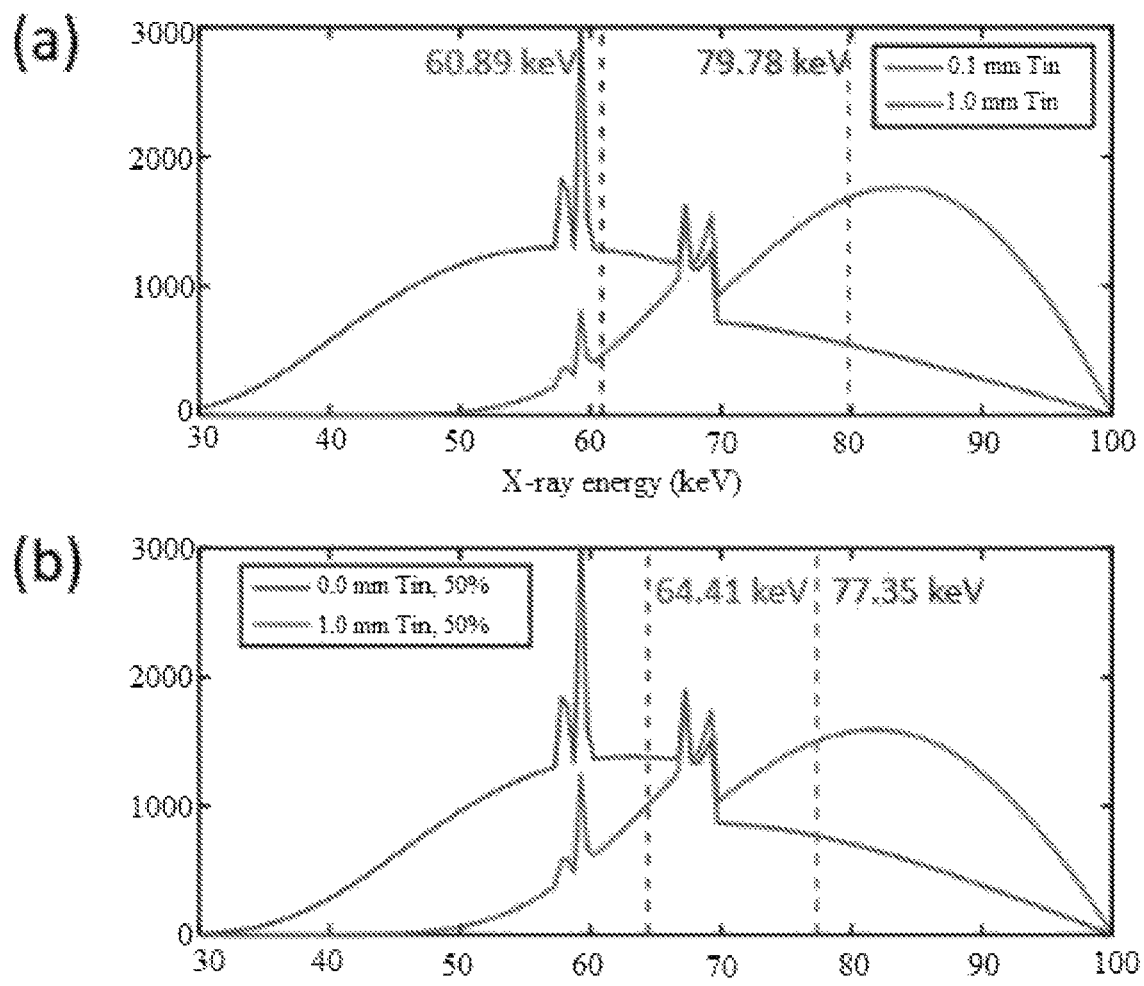
FIG. 7A shows a plot of spectral distributions for a two-strip grating.
FIG. 7B shows a plot of spectral distributions for a multi-strip grating.

FIGS. 7A and 7B show plots of spectral distribution for a $GOLF_c$ setup for a two-strip grating and a multi-strip (more than two-strip) grating, respectively, according to an embodiment of the subject invention. To obtain the plots in FIGS. 7A and 7B, the two types of filtering materials were 0-mm titanium (air) and 1.0-mm titanium materials. In FIGS. 7A and 7B, vertical dotted lines indicate corresponding mean energies (also labeled on the plots), and in each of these plots, the right-most plotted line is for 1.0 mm tin (50% duty cycle in FIG. 7B). In FIG. 7A, the left-most plotted line is for 0.1 mm tin, and in FIG. 7B, the left-most plotted line is for 0.0 mm tin at 50% duty cycle. More generally, in $GOLF_c$ the two-strip filter can be replaced by a grating comprising alternating strips, coupled with an absorption grating as described with reference to $GOLF_k$. With this grating method, the relative displacement between the X-ray focal spot and the filter grating is not needed because the motion of the absorption grating defines the filtration for the X-ray beam. However, the drawback of the grating method is its low X-ray flux efficiency. FIG. 7B is based on a multi-strip grating including 0-mm titanium (air) and 1.0-mm titanium materials with a duty cycle of 50%.

The $GOLF_c$ systems and methods described herein can be used with a conventional X-ray source that does not include kVp-switching, thereby relaxing the need for a kVp-switching X-ray source. However, dynamic relative grating displacement can still be used to select X-ray filtration effects. The dual-energy imaging system can be further simplified with a stationary filtering grating alone or just a stationary two-strip filter where an X-ray imaging model is necessary to separate mixed spectra for hybrid imaging reconstruction (see also, e.g., reference [22] in the References section, which is hereby incorporated herein by reference in its entirety). The stationary filtering grating methods can be referred to as "$GOLF_s$".

A monochromatic image can be reconstructed in both the projection and image domains (see, e.g., references [8] and [23] in the References section, both of which are hereby incorporated herein by reference in their entireties). This is based on the assumption that any material can be represented as a linear combination of two basis materials:

$$\mu^i = \left(\frac{\mu}{\rho}\right)^i_1 \rho_1 + \left(\frac{\mu}{\rho}\right)^i_2 \rho_2, i = L, H \quad (1)$$

where "L" and "H" indicate low- and high-energy, respectively, and "1" and "2" indicate the two basis materials, respectively. Mass densities ($p_1$, $p_2$) of the two basis materials are used to characterize any material. In the projection domain (p) and image domain (p), there are low- and high-energy datasets and images ($p^L$, $p^H$ and $\mu^L$, $\mu^H$). The monochromatic image CT(E) at any x-ray energy E can be reconstructed from projections.

$$P(E) = w(E) \cdot P^L + (1 - w(E)) \cdot P^H. \quad (2)$$

Specifically, $$CT(E) = \text{recon}(P(E)) \quad (3)$$

and $$CT(E) = w(E) \cdot CT^L + (1 - w(e)) \cdot CT^H, \quad (4)$$

where the weighting factor is $$w(E) = \frac{\mu_1(E) \cdot \mu_2^H - \mu_2(E) \cdot \mu_1^H}{\mu_1^L \cdot \mu_2^H - \mu_1^H \cdot \mu_2^L} \cdot \frac{\mu_2^L}{\mu_2(E)}. \quad (5)$$

Systems and method of embodiments of the subject invention, in combination with single-kVp imaging and kVp-switching technology, open new doors to extract dual energy data effectively, with flexibility, and improved cost-effectiveness. The key feature of dual-energy CT imaging is the spectral separation that helps avoid spectral mixing and reveals more information regarding material composition and monochromatic imaging. Systems and method of embodiments of the subject invention can take advantage of these attributes of dual-energy CT imaging while also addressing the motion artifact problem with a dual-source scanner and the spectral overlapping problem with kVp-switching and dual-layer detection systems.

Three main types of GOLF systems and method have been described, including $GOLF_k$, $GOLF_c$, and $GOLF_s$. $GOLF_k$ performs the best in terms of spectral separation, and a combination of absorption grating(s) and filter grating(s) can be used with a single-source CT system to achieve dual-source, dual-energy CT performance similar to that in a $GOLF_c$ system/method. When a kVp-switching X-ray source cannot be used, a $GOLF_c$ or $GOLF_s$ system/method can be used to significantly improve spectral separation. $GOLF_s$ can be thought of as the simplest case of $GOLF_c$ with the highest photon utilization. $GOLF_s$ can work in a stationary mode with only one filter grating, for example in a full scan. The image reconstruction algorithm for $GOLF_s$ can be based on a non-linear X-ray data generation model.

Embodiments of the subject invention can include dynamically modulating the filter grating of millimeter-/sub-millimeter-sized filtering strips by a matching absorption grating with a small oscillation amplitude at a high frequency. Due to this micro-technology, the medical CT requirements for full coverage over the field of view and a rapid change in filtration settings can be simultaneously achieved to yield superior spectral filtration. The filter vibration can be driven by, for example, a piezo-electrical device, which is a mature technology compatible with CT scanning. The use of an absorption grating does result in the loss of some X-ray flux from the source. The duty cycle of the absorption grating can balance the X-ray spectral separation and the X-ray flux utilization. If the duty cycle of the absorption grating is 100% (r=100%), the system is equivalent to a conventional kVp-switching based dual-energy CT; while as r gets closer to 0, spectral separation gain is increased while more X-rays are blocked (X-ray flux decreases). Better spectral separation (narrower opening slits) leads to better quality of reconstructed monochromatic images without having to increase the radiation dose to which the patient (e.g., a mammal such as a human) or subject is exposed during imaging.

In $GOLF_s$ systems and methods according to embodiments of the subject invention, a filter grating can be used with no absorption grating, thereby not completely blocking the path of any X-rays. The image reconstruction from data collected with $GOLF_s$ can be more complicated, involving non-linear data modeling and compressed sensing (see also reference [22] from the References section, which is hereby incorporated herein by reference in its entirety). Spectral mixing in multiple penumbras could be an issue.

It is emphasized that in addition to the explicitly described designs, many variations are possible in the spirit of the invention. For example, the gratings can be made in 2D instead of 1D (e.g., to fit into cone-beam geometry). Also, more than two filtering material types can be introduced (e.g., for multi-energy x-ray imaging). Also, X-ray path lengths in the patient body can be taken into account so that the final diagnostic performance can be optimized instead of the spectral separation itself, which is an indirect measure anyway.

Embodiments of the subject invention can advantageously be used with existing X-ray CT systems with minimal overhead expense. The imaging performance can be improved significantly in terms of monochromatic image quality, material decomposition, and radiation dose reduction. Although the use of an absorption grating can decrease the efficiency of the X-ray source, patient radiation dose is not increased, so this is not a major drawback.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1. A system for performing X-ray computed tomography (CT) imaging, the system comprising:

an X-ray source;

a detector for detecting X-ray radiation from the source;

a filter grating disposed between the source and the detector (to modify the original X-ray energy spectrum of the X-ray radiation of the X-ray source into two or more spectra), wherein the filter grating is positioned closer to the source than the detector is; and an absorption grating aligned with the filter grating (either before the filter grating or after the filter grating, along a path of X-ray radiation from the source to the detector) (to selectively block at least a portion of the X-ray radiation from reaching the filter grating so that a preferred X-ray spectrum can pass through the filter grating and can go through a patient or subject to be imaged at a given time instant), wherein at least one of the absorption grating and the filter grating is configured to move relative to the other during operation of the source.

Embodiment 2. The system according to embodiment 1, wherein the source is a kVp-switching X-ray source.

Embodiment 3. The system according to embodiment 2, wherein the absorption grating and the filter grating oscillate relative one another, and the oscillation is synchronized with a switching frequency of the source, such that each time the source switches its voltage level, at least one of the absorption grating and the filter grating moves relative to the other.

Embodiment 4. The system according to any of embodiments 2-3, wherein an oscillation period of the relative movement between the gratings is equal to half a time interval between two adjacent X-ray projections of the source.

Embodiment 5. The system according to embodiment 1, wherein the source is a single-kVp X-ray source (non-kVp-switching X-ray source).

Embodiment 6. The system according to embodiment 5, wherein the relative movement of the gratings is an oscillation movement (relative to each other) that is optimized for the single-kVp X-ray source.

Embodiment 7. The system according to any of embodiments 1-6, wherein the filter grating comprises at least two different types of filter material.

Embodiment 8. The system according to any of embodiments 1-7, wherein the filter grating comprises exactly two different types of filter material.

Embodiment 9. The system according to any of embodiments 1-8, wherein the absorption grating comprises slit portions and solid portions disposed alternatingly.

Embodiment 10. The system according to embodiment 9, wherein a width of each slit portion of the absorption grating is the same as that of each other slit portion of the absorption grating.

Embodiment 11. The system according to any of embodiments 9-10, wherein a width of each solid portion of the absorption grating is the same as that of each other solid portion of the absorption grating.

Embodiment 12. The system according to any of embodiments 9-11, wherein a width of each slit portion of the absorption grating is the same as that of each solid portion of the absorption grating.

Embodiment 13. The system according to any of embodiments 9-11, wherein a width of at least one slit portion of the absorption grating is different from that of at least one solid portion of the absorption grating.

Embodiment 14. The system according to any of embodiments 9-11, wherein a width of at least one slit portion of the absorption grating is narrower than that of at least one solid portion of the absorption grating.

Embodiment 15. The system according to any of embodiments 9-11, wherein a width of at least one slit portion of the absorption grating is wider than that of at least one solid portion of the absorption grating.

Embodiment 16. The system according to any of embodiments 9-11, wherein a width of each slit portion of the absorption grating is narrower than that of at least one solid portion of the absorption grating.

Embodiment 17. The system according to any of embodiments 9-11, wherein a width of each slit portion of the absorption grating is wider than that of at least one solid portion of the absorption grating.

Embodiment 18. The system according to any of embodiments 9-11, wherein a width of each slit portion of the absorption grating is narrower than that of each solid portion of the absorption grating.

Embodiment 19. The system according to any of embodiments 9-11, wherein a width of each slit portion of the absorption grating is wider than that of each solid portion of the absorption grating.

Embodiment 20. The system according to any of embodiments 9-11, wherein a width of at least one slit portion of the absorption grating is narrower than that of each solid portion of the absorption grating.

Embodiment 21. The system according to any of embodiments 9-11, wherein a width of at least one slit portion of the absorption grating is wider than that of each solid portion of the absorption grating.

Embodiment 22. The system according to any of embodiments 1-21, wherein the relative motion between the absorption grating and the filter grating is in a direction parallel to a front face of the absorption grating facing the source.

Embodiment 23. The system according to any of embodiments 1-22, wherein the absorption grating comprises a metal.

Embodiment 24. The system according to any of embodiments 1-23, wherein the absorption grating comprises gold.

Embodiment 25. The system according to any of embodiments 1-24, wherein a thickness of the absorption grating is 1 mm.

Embodiment 26. The system according to any of embodiments 1-24, wherein a thickness of the absorption grating is at least 1 mm.

Embodiment 27. The system according to any of embodiments 1-24, wherein a thickness of the absorption grating is no more than 1 mm.

Embodiment 28. The system according to any of embodiments 1-24, wherein a thickness of the absorption grating is 0.5 mm.

Embodiment 29. The system according to any of embodiments 1-24, wherein a thickness of the absorption grating is at least 0.5 mm.

Embodiment 30. The system according to any of embodiments 1-24, wherein a thickness of the absorption grating is no more than 0.5 mm.

Embodiment 31. The system according to any of embodiments 1-30, wherein the filter grating comprises a first filter material and a second filter material that is less dense than the first filter material.

Embodiment 32. The system according to embodiment 31, wherein the first filter material is a metal air and the second filter material is air.

Embodiment 33. The system according to any of embodiments 31-32, wherein the first filter material is tin.

Embodiment 34. The system according to any of embodiments 31-33, wherein the filter grating comprises a plurality of strips of the second filter material, with the first filter material disposed alternatingly with the plurality of strips of the second filter material.

Embodiment 35. The system according to any of embodiments 1-34, wherein a thickness of the filter grating is 1 mm.

Embodiment 36. The system according to any of embodiments 1-34, wherein a thickness of the filter grating is at least 1 mm.

Embodiment 37. The system according to any of embodiments 1-34, wherein a thickness of the filter grating is no more than 1 mm.

Embodiment 38. The system according to any of embodiments 1-34, wherein a thickness of the filter grating is 0.5 mm.

Embodiment 39. The system according to any of embodiments 1-34, wherein a thickness of the filter grating is at least 0.5 mm.

Embodiment 40. The system according to any of embodiments 1-34, wherein a thickness of the filter grating is no more than 0.5 mm.

Embodiment 41. The system according to any of embodiments 1-40, wherein the filter grating moves while the absorption grating stays stationary during operation of the source.

Embodiment 42. The system according to any of embodiments 1-40, wherein the absorption grating moves while the filter grating stays stationary during operation of the source.

Embodiment 43. The system according to any of embodiments 1-40, wherein both the absorption grating and the filter grating move during operation of the source.

Embodiment 44. The system according to any of embodiments 1-43, further comprising a motor configured to move at least one of the absorption grating and the filter grating relative to the other during operation of the source.

Embodiment 45. The system according to embodiment 44, wherein the motor is a piezo-electrical motor.

Embodiment 46. The system according to any of embodiments 1-45, wherein the absorption grating has a curved geometry.

Embodiment 47. The system according to any of embodiments 1-46, wherein the filter grating has a curved geometry.

Embodiment 48. The system according to any of embodiments 1-47, wherein the filter grating is disposed between the source and a patient to be imaged.

Embodiment 49. The system according to any of embodiments 1-48, wherein a distance between the filter grating and the source is less than 1 meter.

Embodiment 50. The system according to any of embodiments 1-48, wherein a distance between the filter grating and the source is less than 500 mm.

Embodiment 51. The system according to any of embodiments 1-48, wherein a distance between the filter grating and the source is less than 250 mm.

Embodiment 52. The system according to any of embodiments 1-51, wherein the source is an X-ray tube.

Embodiment 53. A method of performing X-ray CT imaging, the method comprising:
providing the system according to any of embodiments 1-52 and 94-96;
positioning a patient or sample to be imaged between the filter grating and the detector;
operating the source to provide X-ray radiation; and
moving at least one of the filter grating and the absorption grating relative to the other during operation of the source.

Embodiment 54. The method according to embodiment 53, wherein the filter grating moves while the absorption grating stays stationary during operation of the source.

Embodiment 55. The method according to embodiment 53, wherein the absorption grating moves while the filter grating stays stationary during operation of the source.

Embodiment 56. The method according to embodiment 53, wherein both the absorption grating and the filter grating move during operation of the source.

Embodiment 57. The method according to any of embodiments 53-56, wherein the source is a kVp-switching X-ray source, and wherein an oscillation period of the relative movement between the gratings is equal to half a time interval between two adjacent X-ray projections of the source.

Embodiment 58. The method according to any of embodiments 53-56, wherein the source is a single-kVp X-ray source, and wherein the relative movement of the gratings is an oscillation movement (relative to each other) that is optimized for the single-kVp X-ray source.

Embodiment 59. The method according to any of embodiments 53-58, wherein the patient is a mammal.

Embodiment 60. The method according to any of embodiments 53-59, wherein the patient is a human.

Embodiment 61. A system for performing X-ray computed tomography (CT) imaging, the system comprising:
a single-kVp X-ray source (non-kVp-switching X-ray source);
a detector for detecting X-ray radiation from the source; and
a filter grating disposed between the source and the detector (to modify the original X-ray energy spectrum of the X-ray radiation of the X-ray source into two or more spectra), wherein the filter grating is positioned closer to the source than the detector is,
wherein the system excludes an absorption grating, and
wherein the filter grating is configured to be stationary during operation of the source.

Embodiment 62. The system according to embodiment 61, wherein the filter grating comprises at least two different types of filter material.

Embodiment 63. The system according to any of embodiments 61-62, wherein the filter grating comprises exactly two different types of filter material.

Embodiment 64. The system according to any of embodiments 61-63, wherein the filter grating comprises at least two filter strips.

Embodiment 65. The system according to any of embodiments 61-63, wherein the filter grating comprises exactly two filter strips.

Embodiment 66. The system according to embodiment 65, wherein the two filter strips comprise a first filter strip of a first filter material and a second filter strip of a second filter material different from the first filter material.

Embodiment 67. The system according to embodiment 66, wherein the first filter material is a metal air and the second filter material is air.

Embodiment 68. The system according to any of embodiments 66-67, wherein the first filter material is tin.

Embodiment 69. The system according to any of embodiments 61-64, wherein the filter grating comprises a first filter material and a second filter material that is less dense than the first filter material.

Embodiment 70. The system according to embodiment 69, wherein first filter material is a metal and the second filter material is air.

Embodiment 71. The system according to any of embodiments 69-70, wherein the first filter material is tin.

Embodiment 72. The system according to any of embodiments 69-71, wherein the first and second filter materials are disposed alternatingly in the filter grating.

Embodiment 73. The system according to any of embodiments 61-72, wherein a thickness of the filter grating is 1 mm.

Embodiment 74. The system according to any of embodiments 61-72, wherein a thickness of the filter grating is at least 1 mm.

Embodiment 75. The system according to any of embodiments 61-72, wherein a thickness of the filter grating is no more than 1 mm.

Embodiment 76. The system according to any of embodiments 61-72, wherein a thickness of the filter grating is 0.5 mm.

Embodiment 77. The system according to any of embodiments 61-72, wherein a thickness of the filter grating is at least 0.5 mm.

Embodiment 78. The system according to any of embodiments 61-72, wherein a thickness of the filter grating is no more than 0.5 mm.

Embodiment 79. The system according to any of embodiments 61-78, wherein the filter grating has a curved geometry.

Embodiment 80. The system according to any of embodiments 61-79, wherein the filter grating is disposed between the source and a patient to be imaged.

Embodiment 81. The system according to any of embodiments 61-80, wherein a distance between the filter grating and the source is less than 1 meter.

Embodiment 82. The system according to any of embodiments 61-80, wherein a distance between the filter grating and the source is less than 500 mm.

Embodiment 83. The system according to any of embodiments 61-80, wherein a distance between the filter grating and the source is less than 250 mm.

Embodiment 84. The system according to any of embodiments 61-83, wherein the source is an X-ray tube.

Embodiment 85. A method of performing X-ray CT imaging, the method comprising:
providing the system according to any of embodiments 61-84 and 96;
positioning a patient or sample to be imaged between the filter grating and the detector; and
operating the source to provide X-ray radiation.

Embodiment 86. The method according to embodiment 85, wherein the patient is a mammal.

Embodiment 87. The method according to any of embodiments 85-86, wherein the patient is a human.

Embodiment 88. The system according to any of embodiments 1-52 and 61-84, further comprising:
a processor; and
a (non-transitory) machine-readable medium (e.g., a computer-readable medium) in operable communication with both the processor and the detector and having machine-executable (e.g., computer-executable) instructions (stored thereon) for image reconstruction based on data received from the detector.

Embodiment 89. The system according to embodiment 88, wherein the image reconstruction is based on a non-linear X-ray data generation model.

Embodiment 90. The system according to any of embodiments 88-89, wherein the image reconstruction comprises non-linear data modeling and compressed sensing.

Embodiment 91. The method according to any of embodiments 53-60 and 85-87, wherein the system further comprises:
a processor; and
a (non-transitory) machine-readable medium (e.g., a computer-readable medium) in operable communication with both the processor and the detector and having machine-executable (e.g., computer-executable) instructions (stored thereon) for image reconstruction based on data received from the detector, and wherein the method further comprises performing the image reconstruction.

Embodiment 92. The method according to embodiment 91, wherein the image reconstruction is based on a non-linear X-ray data generation model.

Embodiment 93. The method according to any of embodiments 91-92, wherein the image reconstruction comprises non-linear data modeling and compressed sensing.

Embodiment 94. The system according to any of embodiments 1-52, and 88-90, wherein the absorption grating is disposed between the filter grating and the source.

Embodiment 95. The system according to any of embodiments 1-52, 61-84, and 88-90, wherein the filter grating is disposed between the absorption grating and the source.

Embodiment 96. The system according to any of embodiments 1-52, 61-84, 88-90, 94, and 95, wherein the filter grating is positioned closer to the source than it is to the detector.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Simulation Parameters

Numerical simulations were carried out to evaluate GOLF systems and methods of embodiments of the subject invention, both for kVp-switching and non-kVp-switching dual-energy CT systems. Water and bone were selected as basis materials, and images were reconstructed via conventional filtered-back-projection without pre- and post-processing steps. A CT imaging simulation platform was implemented to evaluate the performance of the proposed filtration methods. In the simulation, 140 kVp was set for single-kVp (non-kVp-switching) dual-energy CT, and 80 kVp and 140 kVp X-rays were used for kVp-switching dual-energy CT scanning. For both kVp settings, 100,000 photons were generated, and Poisson noise was added into the projections. In the CT geometry, the distance between the X-ray focal spot and the rotation center was set to 500 mm, and the distance between the X-ray focal spot and the flat-panel detector was set to 900 mm. There were 888 channels in the detector array with cell size of 1 mm. The field-of view was set to 320 mm with 512×512 pixels and 0.625 mm pixel size. The chest phantom depicted in FIG. 8 was used, in which titanium-material rods were inserted, as indicated by the large (white) dots near the bottom middle of the phantom.

Figure 8:
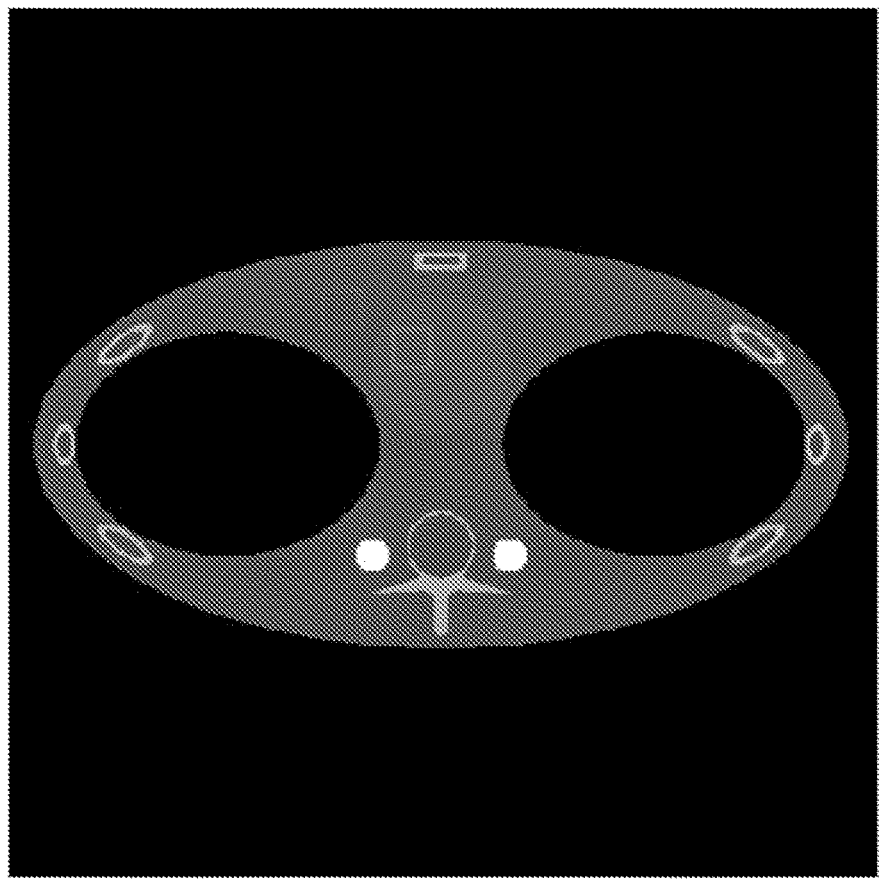
FIG. 8 shows a chest phantom.

The signal-to-noise ratio (SNR) is defined as $$\frac{(\overline{A}_{blue} - \overline{A}_{red})}{\sqrt{\sigma^2_{Ablue} + \sigma^2_{Ared}}}, \qquad (6)$$

where $\overline{A}$ is the average over a region of interest (ROI), and $\sigma$ is the standard variation in the ROI, to quantify a monochromatic image. In FIG. 8, two squares are included in the upper-middle area of the phantom; these boxes are ROIs of 30×30 pixels.

These conditions and parameters were for all numerical simulation examples.

Example 1

A GOLF$_k$ system/method was simulated for kVp-switching based dual-energy CT. In a CT scan, 1,440 projections were collected where half of the data were at 80 kVp and the other half were at 140 kVp. The filter grating used 0.0 mm (air) and 1.0 mm thick tin with a duty cycle of 50%. The thickness of the X-ray absorption grating was 1 mm gold material allowing 99.995% absorption of X-rays at 100 keV. The duty cycle was changed from 10% to 100%, with a duty cycle of 100% being equivalent to conventional kVp-switching imaging. The monochromatic images were reconstructed according to Equation 4.

Figure 9:
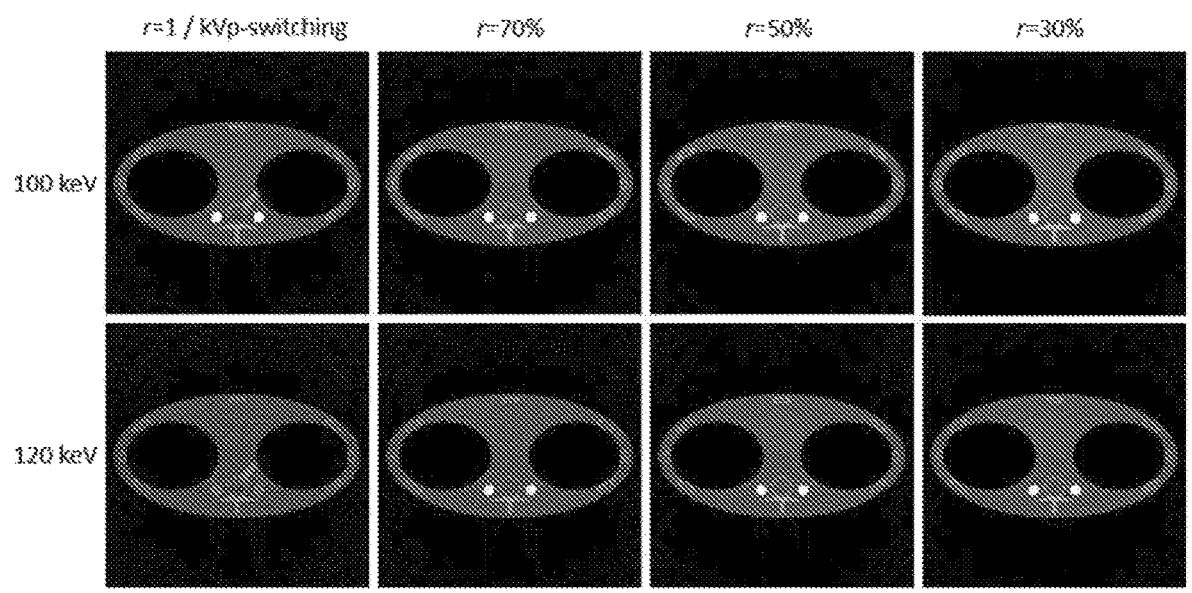
FIG. 9 shows eight reconstructed monochromatic images from a numerical simulation of CT scans.
Figure 10:
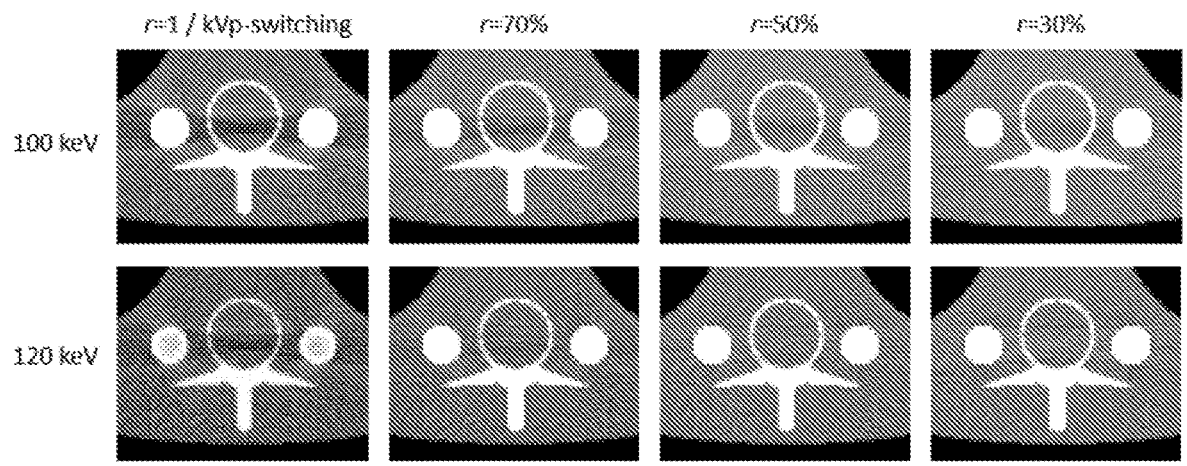
FIG. 10 shows eight enlarged images of the local metal areas (the areas around the rods represented by the dots near the lower-middle section of the phantom) of the corresponding images from FIG. 9.
Figure 13:
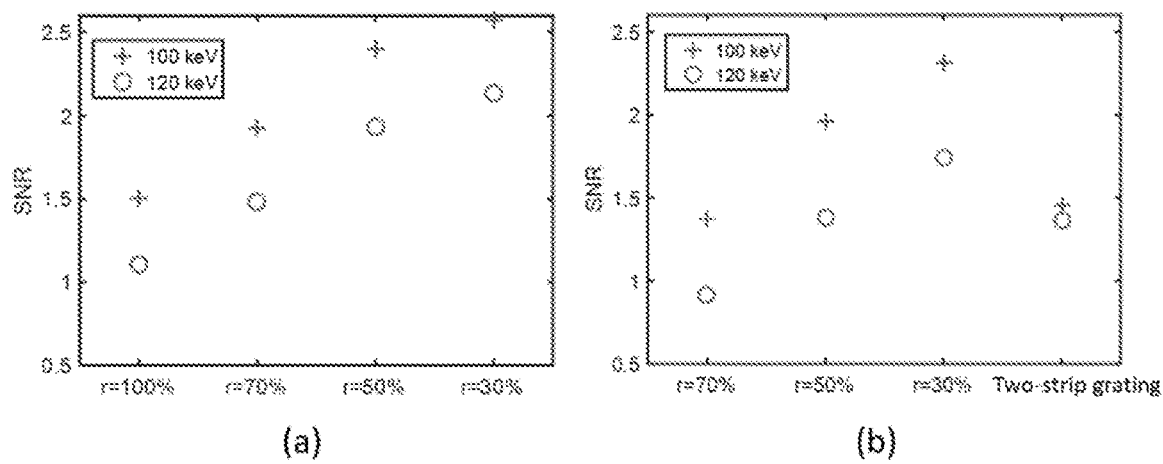
FIG. 13A shows a plot of signal-to-noise ratio (SNR) for the images of FIG. 9.
FIG. 13B shows a plot of SNR for the images of FIG. 11.

FIG. 9 shows the reconstructed monochromatic images for this example. In FIG. 9, the first row presents images at 100 keV at different absorption grating duty cycles, as listed above each column. The first column is for a duty cycle of 100% (equivalent to conventional kVp-switching imaging). The second row shows results at 120 keV at different absorption grating duty cycles. FIG. 10 shows the local metal areas (the areas around the rods represented by the dots near the lower-middle section of the phantom) of the images from FIG. 9. The rows and columns in FIG. 10 are for the same energy/duty cycle combinations as in FIG. 9. FIG. 13A shows the SNR values for the images of FIG. 9. In FIG. 13A, the cross data points are for an energy of 100 keV, the circle data points are for an energy of 120 keV, the y-axis shows the SNR, and the x-axis shows the different duty cycles investigated.

Referring to FIGS. 9 and 10, the first column for each shows the performance that is equivalent to conventional kVp-switching dual-energy CT. There are clear beam hardening artifacts indicated by the (red) arrow present in each image in the first column of FIG. 9, and this can be seen more clearly in the enlarged views in the first column of FIG. 10. At the same location in the images in the second, third, and fourth columns of these figures, significantly less artifacts are present, and the best performance was for r=30%. Referring to FIG. 13A, with a smaller absorption grating opening, the low- and high-energy X-ray spectra have better separation, leading to better image quality, in particular in terms of beam-hardening reduction.

Example 2

A $GOLF_c$ system/method was simulated for single-kVp-based (non-kVp-switching) dual-energy CT. In a CT scan, 1,440 projections were collected at 140 kVp. The filter grating used 0.1-mm tin and 1.0-mm tin in the two strip filter, and 0.0-mm tin (air) and 1.0-mm tin with 50% duty cycle in the multi-strip grating. The monochromatic images were reconstructed according to Equation 4.

Figure 11:
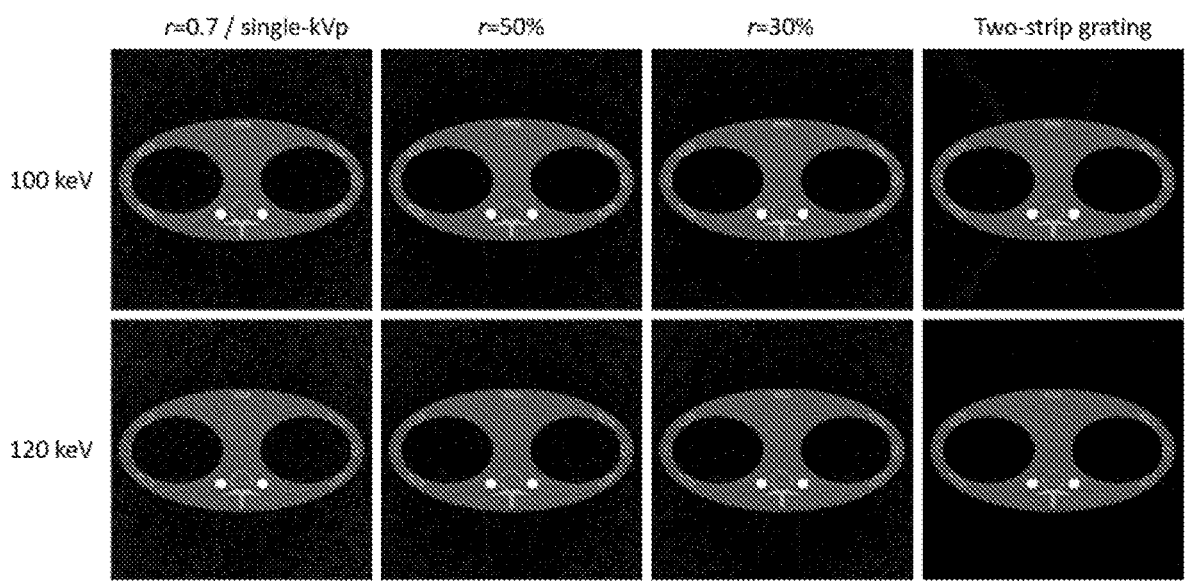
FIG. 11 shows eight reconstructed monochromatic images from a numerical simulation of CT scans.
Figure 12:
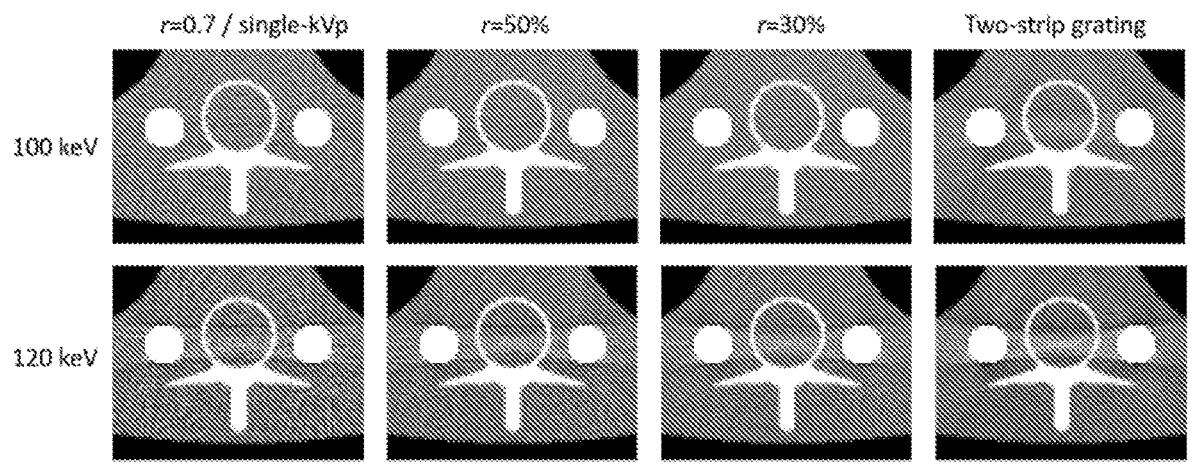
FIG. 12 shows eight enlarged images of the local metal areas (the areas around the rods represented by the dots near the lower-middle section of the phantom) of the corresponding images from FIG. 11.

FIG. 11 shows the reconstructed monochromatic images for this example. In FIG. 11, the first row presents images at 100 keV at different absorption grating duty cycles for multi-strip gratings (in the first three columns) and for a two-strip grating (in the fourth column), as listed above each column. The second row shows results at 120 keV. FIG. 12 shows the local metal areas (the areas around the rods represented by the dots near the lower-middle section of the phantom) of the images from FIG. 11. The rows and columns in FIG. 12 are for the same energy/duty cycle combinations as in FIG. 11. FIG. 13B shows the SNR values for the images of FIG. 11. In FIG. 13B, the cross data points are for an energy of 100 keV, the circle data points are for an energy of 120 keV, the y-axis shows the SNR, and the x-axis shows the different duty cycles investigated for the multi-strip gratings (first three marks on x-axis) and the two-strip grating (right-most mark on x-axis).

Referring to FIGS. 11 and 12, there are some artifacts in the central area of the images with the two-strip grating method (far right column in each of FIGS. 11 and 12). They were caused by the data interpolation in the sinogram, which can be avoided by advanced algorithms, such as iterative reconstruction schemes (see also reference [24] in the References section, which is hereby incorporated herein by reference in its entirety). Overall, the two-strip grating approach has a similar performance to that of the 50% duty cycle multi-strip grating approach.

Comparing the $GOLF_c$ method/system of this example to the $GOLF_k$ method/system of Example 1, the kVp-switching method results in better performance across the board in terms of beam-hardening reduction and SNR, which is consistent with its improved spectrum separation demonstrated by comparing FIGS. 5A-5C with FIGS. 7A-7B. Also, with the $GOLF_k$ system/method, a smaller absorption grating opening (smaller duty cycle) leads to SNR performance for a given radiation dose to the patient, but at the same time reduces the X-ray source efficacy.

Example 3

A $GOLF_k$ system/method was simulated for kVp-switching based dual-energy CT, including collecting 360, 720, 1080 projections of each energy X-rays in turn. The thickness of the X-ray absorption grating was 1 mm gold materials having 99.995% absorption of X-rays at 100 keV. In the filter grating, the two filtration materials for 80 kVp and 140 kVp X-rays were air and tin, respectively. The thickness of tin material was set to 0 mm, 0.25 mm, and 0.5 mm in different experiments. The vibration frequency of the filter grating was set to match the switching frequency of X-ray energies in the X-ray source.

Figure 14:
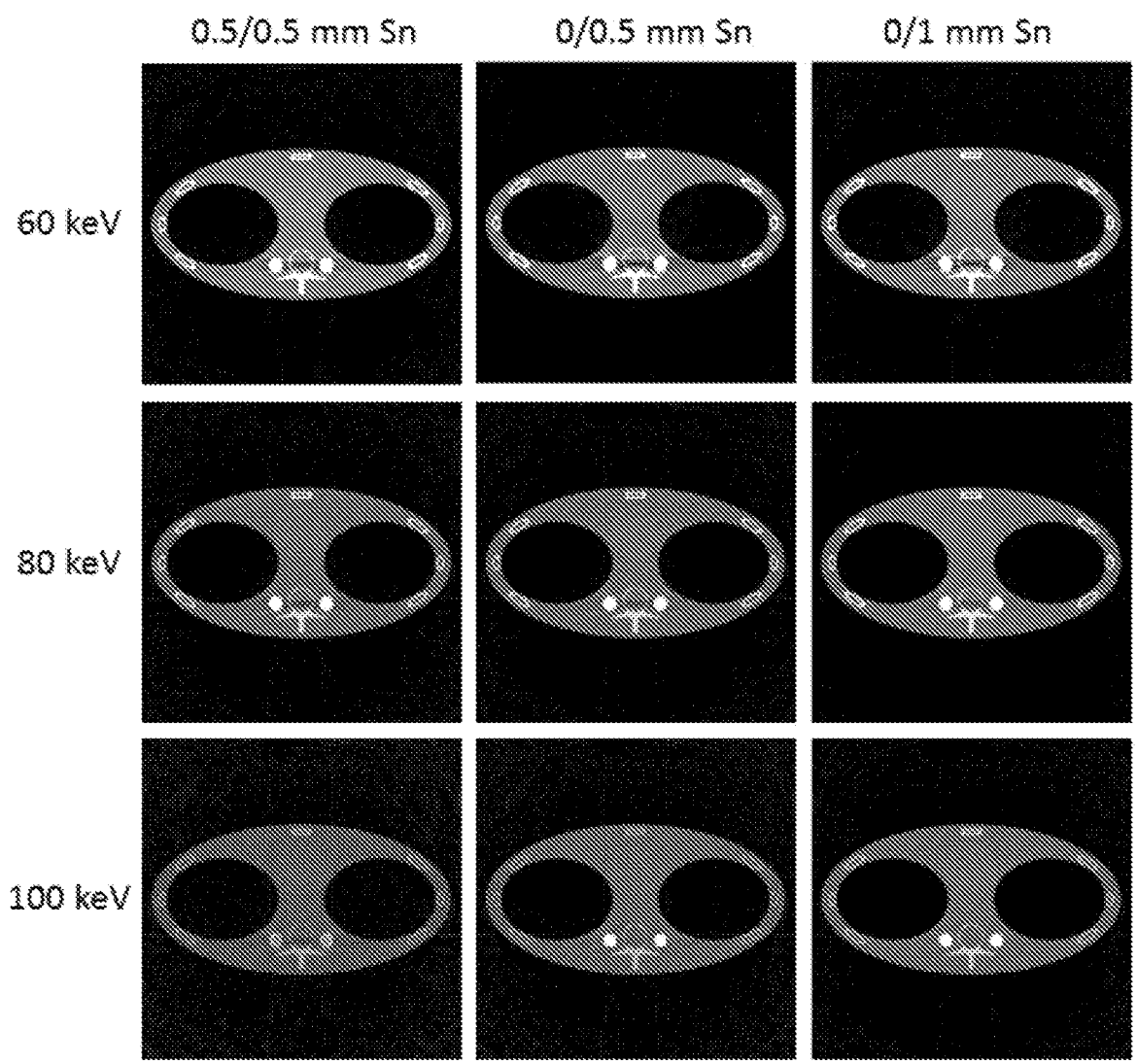
FIG. 14 shows nine reconstructed monochromatic images from a numerical simulation of CT scans.
Figure 15:
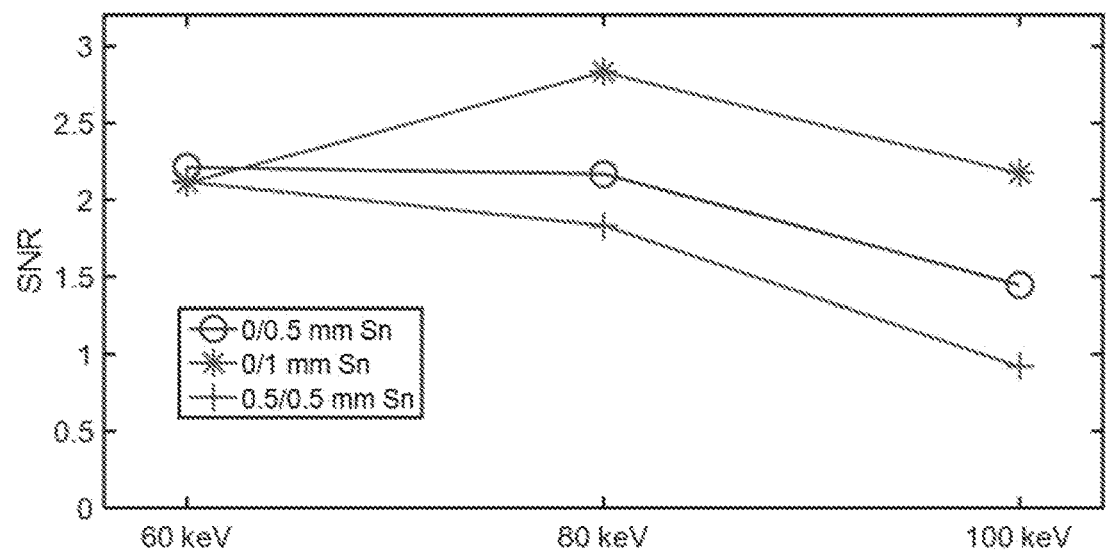
FIG. 15 shows a plot of SNR versus energy for the images of FIG. 14.

FIG. 14 shows the reconstructed monochromatic images. The first column presents images at energies of 60 keV, 80 keV and 100 keV (in the first, second, and third rows, respectively) with 0.5 mm tin and 0.5 mm tin (i.e., a conventional kVp-switching method). The right-most columns show the results for air and 0.5 mm tin (middle column) and air and 1 mm tin (right-most column). FIG. 15 shows a plot of SNR for these images. The cross data points are for the conventional kVp-switching method, the circle data points are for the air/1 mm tin $GOLF_k$ system/method, and the star data points are for the air/0.5 mm tin $GOLF_k$ system/method. The upper-most (green) line shows connects the star data points, the middle-most (red) line connects the circle data points, and the lower-most (blue) line connects the cross data points.

Referring to FIGS. 14 and 15, it can be plainly seen that the GOLFk system/method leads to much clearer monochromatic images, both visually and quantitatively. The air/0.5 mm tin $GOLF_k$ system/method provides better results than the air/1 mm tin $GOLF_k$ system/method.

Example 4

A $GOLF_k$ system/method was simulated for kVp-switching based dual-energy CT, including collecting 360, 720, 1080 projections of each energy X-rays in turn. The fixed filtration materials were air for 80 kVp X-rays and 0.5 mm tin for 140 kVp X-rays. The distance between focal spots was determined by the geometry of the CT scanner and the angular difference between neighboring projections. In the 360 projection setting, a uniform angular sampling around the circular trajectory was assumed, and the distance between neighboring 80 kVp and 140 kVp X-rays was 4.36 mm. In the X-ray source, the X-ray focal spots and corresponding filters were set to a distance of 4.36 mm accordingly to have the collected neighboring 80 kVp and 140 kVp projection pairs with the same projection angles. Results were obtained using the X-flying focal spot method.

Figure 16:
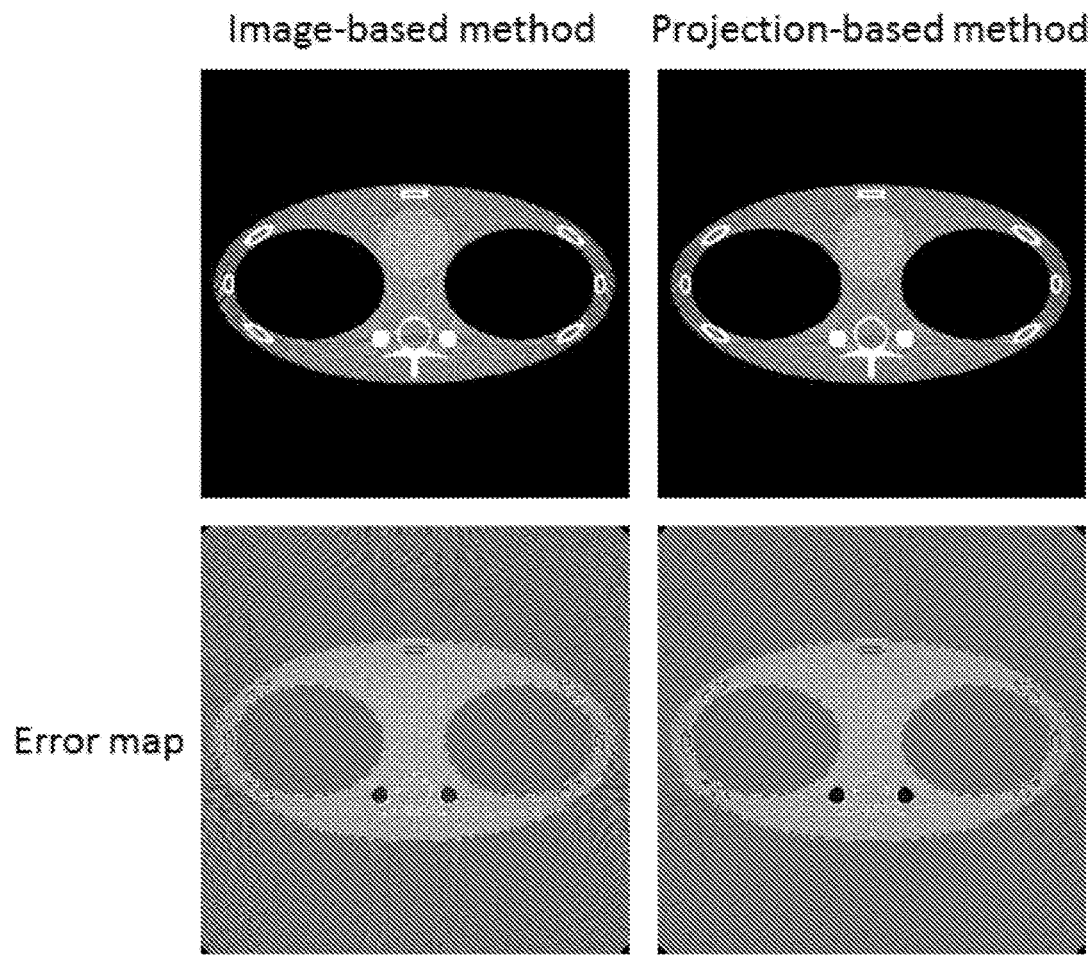
FIG. 16 shows reconstructed monochromatic images from a numerical simulation of CT scans.
Figure 17:
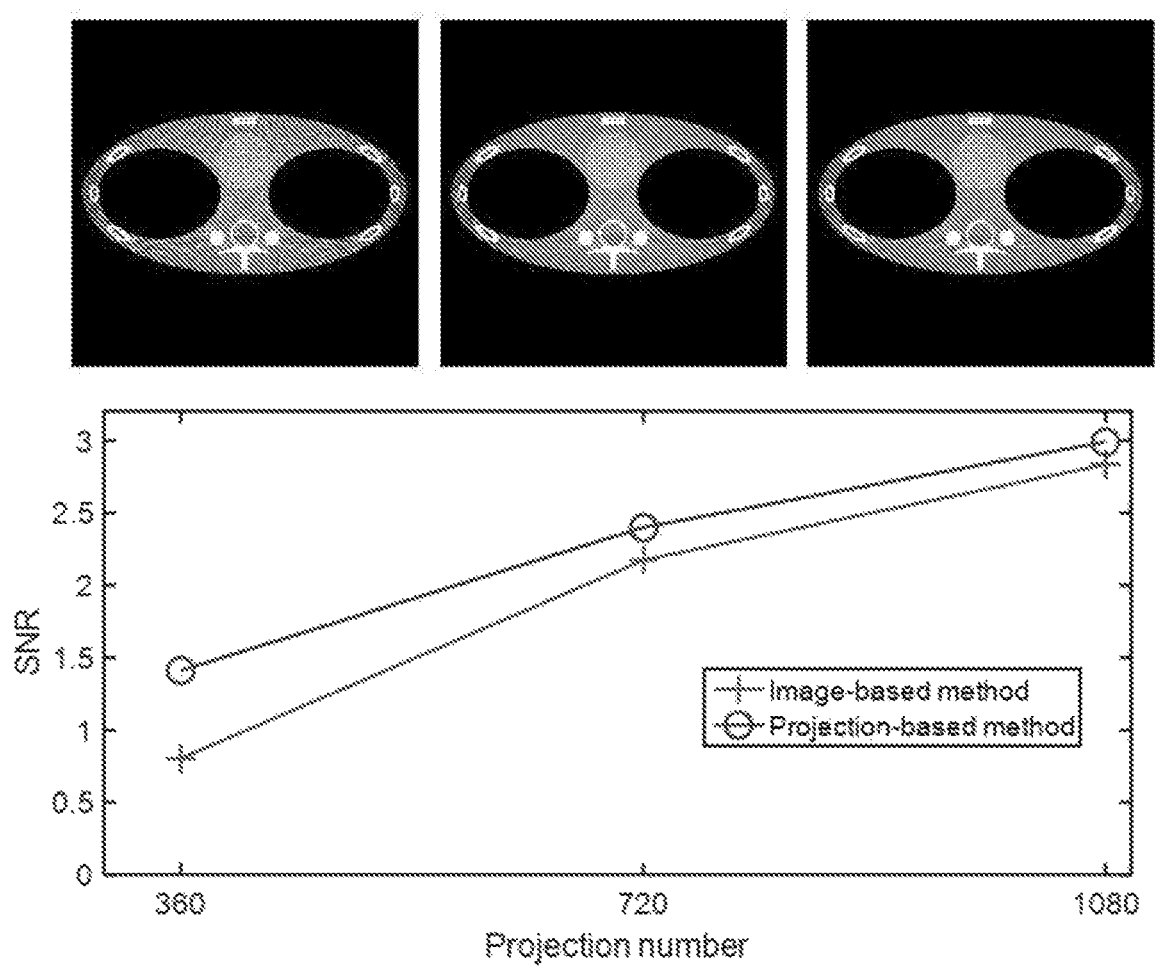
FIG. 17 shows reconstructed monochromatic images from a numerical simulation of CT scans (top portion) and a plot of SNR versus number of projections.

FIG. 16 shows a comparison of the 100 keV, 720-projection 0/0.5 mm Sn image from FIG. 14 for Example 3 (the bottom-middle image in FIG. 14) with the image obtained in this example at 100 keV, 720-projection. The first row shows the images, and the second row shows the error map; the first column is the image from Example 3, and the second column is the image from this example. FIG. 17 shows the images from this example across the top; images left to right are for 360, 720, and 1080 projections (100 keV, 0/0.5 mm Sn), respectively, and the plot at the lower portion of FIG. 17 shows a plot of the SNR vs. projection number. The circle data points are for this example (the three images at the top portion of FIG. 17) and are connected by the upper (red) line, and the cross data points are for Example 3 and are connected by the lower (blue) line. The cross data points are for 100 keV, 0/0.5 Sn at the three different numbers of projections. Referring to FIGS. 16 and 17, it can be seen that a higher number of projections gives a better monochromatic image, and the X-flying focal spot method improves the results slightly.

Example 5

Figure 18:
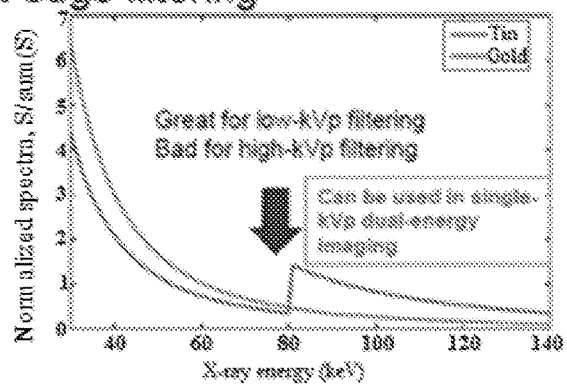
FIG. 18 shows four plots for K-edge filtering, with two plots of normalized spectra versus X-ray energy (top portion) and two plots of spectra versus X-ray energy (lower portion).
Figure 18:
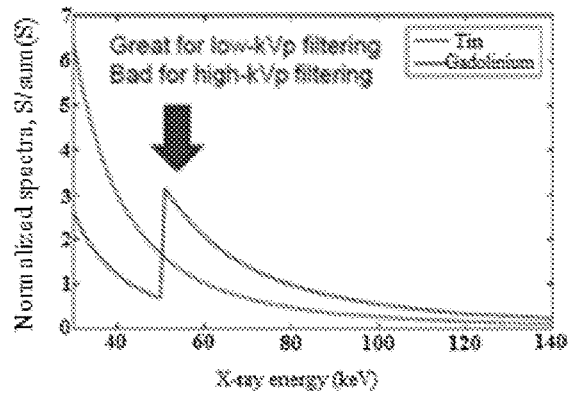
Figure 18:
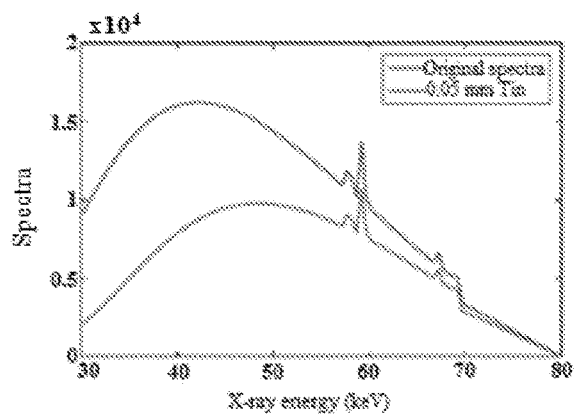
Figure 18:
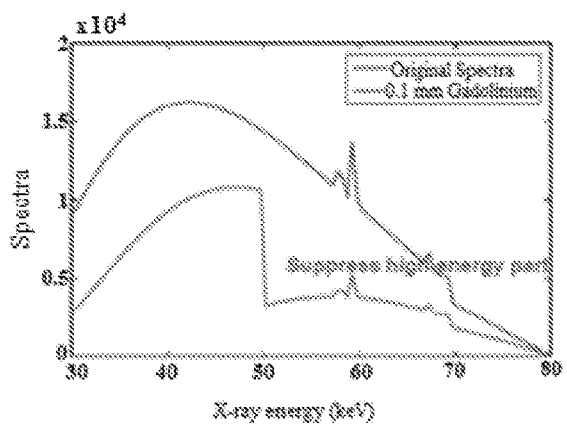

A GOLF system/method was simulated for K-edge filtering. The top portion of FIG. 18 shows plots of normalized spectra versus X-ray energy for tin and gold (top left, with the (blue) line that is higher at the left of the plot being for tin and the (red) line that is higher at the right of the plot being for gold) and for tin and gadolinium (top right, with the (blue) line that is higher at the left of the plot being for tin and the (red) line that is higher at the right of the plot being for gadolinium). The bottom portion of FIG. 18 shows plots of spectra versus X-ray energy for without GOLF ("original") and then using a 0.05 mm tin absorption grating (bottom left, with the (blue) line that is higher at the left of the plot being for the original and the (red) line that is lower at the left of the plot being for 0.5 mm tin) and for original and 0.1 mm gadolinium (bottom right, with the (blue) line that is higher at the left of the plot being for the original and the (red) line that is lower at the left of the plot being for 0.1 mm gadolinium). It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

[1] W. A. Kalender, "X-ray computed tomography," *Physics in medicine and biology*, vol. 51, p. R29, 2006.
[2] G. Wang, H. Yu, and B. De Man, "An outlook on x-ray CT research and development," *Medical physics*, vol. 35, pp. 1051-1064, 2008.
[3] G. Wang, T.-H. Lin, P.-c. Cheng, and D. M. Shinozaki, "A general cone-beam reconstruction algorithm," *Medical Imaging, IEEE Transactions on*, vol. 12, pp. 486-496, 1993.
[4] K. Taguchi and H. Aradate, "Algorithm for image reconstruction in multi-slice helical CT," *Medical Physics*, vol. 25, pp. 550-561, 1998.
[5] G. Wang, C. R. Crawford, and W. A. Kalender, "Guest editorial-Multirow detector and cone-beam spiral/helical CT," *Medical Imaging, IEEE Transactions on*, vol. 19, pp. 817-821, 2000.
[6] T. R. Johnson, B. Krauss, M. Sedlmair, M. Grasruck, H. Bruder, D. Morhard, et al., "Material differentiation by dual energy CT: initial experience," *European radiology*, vol. 17, pp. 1510-1517, 2007.
[7] A. Graser, T. R. Johnson, H. Chandarana, and M. Macari, "Dual energy CT: preliminary observations and potential clinical applications in the abdomen," *European radiology*, vol. 19, pp. 13-23, 2009.
[8] L. Yu, S. Leng, and C. H. Mccollough, "Dual-energy CT-based monochromatic imaging," *Ajr American Journal of Roentgenology*, vol. 199, pp. S9-S15, 2012.
[9] M. Karcaaltincaba and A. Aktaş, "Dual-energy CT revisited with multidetector CT: review of principles and clinical applications," *Diagnostic & Interventional Radiology*, vol. 17, pp. 181-94, 2010.
[10] J. Schlomka, E. Roessl, R. Dorscheid, S. Dill, G. Martens, T. Istel, et al., "Experimental feasibility of multi-energy photon-counting K-edge imaging in pre-clinical computed tomography," *Physics in medicine and biology*, vol. 53, p. 4031, 2008.
[11] W. C. Barber, E. Nygard, J. S. Iwanczyk, M. Zhang, E. C. Frey, B. M. Tsui, et al., "Characterization of a novel photon counting detector for clinical CT: count rate, energy resolution, and noise performance," in *SPIE Medical Imaging*, 2009, pp. 725824-725824-9.
[12] H. Gao, H. Yu, S. Osher, and G. Wang, "Multi-energy CT based on a prior rank, intensity and sparsity model (PRISM)," *Inverse problems*, vol. 27, p. 115012, 2011.
[13] J. Fornaro, S. Leschka, D. Hibbeln, A. Butler, N. Anderson, G. Pache, et al., "Dual- and multienergy CT: approach to functional imaging," *Insights Into Imaging*, vol. 2, pp. 149-159, 2011.
[14] B. Li, G. Yadava, and J. Hsieh, "Quantification of head and body CTDIVOL of dual-energy x-ray CT with fast-kVp switching," *Medical Physics*, vol. 38, pp. 2595-601, 2011.
[15] R. Carmi, G. Naveh, and A. Altman, "Material separation with dual-layer CT," *IEEE Nuclear Science Symposium Conference Record Nuclear Science Symposium*, vol. 4, 2005.
[16] T. G. Flohr, C. H. Mccollough, H. Bruder, M. Petersilka, K. Gruber, C. Suβ, et al., "et al. First performance evaluation of a dualsource CT (DSCT) system," *European Radiology*, vol. 16, pp. 256-68, 2006.
[17] M. Petersilka, H. Bruder, B. Krauss, K. Stierstorfer, and T. G. Flohr, "Technical principles of dual source CT," *European Journal of Radiology*, vol. 68, pp. 362-368, 2008.
[18] M. Grasruck, S. Kappler, M. Reinwand, and K. Stierstorfer, "Dual energy with dual source CT and kVp switching with single source CT: A comparison of dual energy performance," *Proceedings of SPIE—The International Society for Optical Engineering*, vol. 7258, 2009.
[19] T. G. Flohr, K. Stierstorfer, S. Ulzheimer, H. Bruder, A. N. Primak, and C. H. Mccollough, "Image reconstruction and image quality evaluation for a 64-slice CT scanner with z-flying focal spot," *Medical Physics*, vol. 32, pp. 2536-47, 2005.

[20] G. Wang, "X-ray micro-CT with a displaced detector array," *Medical Physics*, vol. 29, pp. 1634-6, 2002.

[21] V. Liu, N. R. Lariviere, and G. Wang, "X-ray micro-CT with a displaced detector array: application to helical cone-beam reconstruction," *Medical Physics*, vol. 30, pp. 2758-61, 2003.

[22] Q. Yang, W. Cong, Y. Xi, and G. Wang, "Spectral X-ray CT Reconstruction with Combination of Energy-integrating and Photon-counting Modules," *Plos ONE*, 2016.

[23] L. Yu, J. A. Christner, S. Leng, J. Wang, J. G. Fletcher, and C. H. Mccollough, "Virtual monochromatic imaging in dual-source dual-energy CT: Radiation dose and image quality," *Medical Physics*, vol. 38, pp. 6371-9, 2011.

[24] M. Beister, D. Kolditz, and W. A. Kalender, "Iterative reconstruction methods in X-ray CT," *Physica Medica*, vol. 28, pp. 94-108, 2012.

[25] M. J. Kang, C. M. Park, C. H. Lee, J. M. Goo, and H. J. Lee, "Dual-energy CT: clinical applications in various pulmonary diseases," *Radiographics*, vol. 30, pp. 685-98, 2010.

[26] Wang et al., International Patent Application Publication No. WO2016/106348.

[27] Wang et al., U.S. Patent Application Publication No. 2015/0157286.

[28] Wang et al., U.S. Patent Application Publication No. 2015/0170361.

[29] Wang et al., U.S. Patent Application Publication No. 2015/0193927.

[30] Wang et al., International Patent Application Publication No. WO2015/164405.

[31] Wang et al., U.S. Patent Application Publication No. 2016/0113602.

[32] Wang et al., U.S. Patent Application Publication No. 2016/0135769.

[33] Wang et al., U.S. Patent Application Publication No. 2016/0166852.

[34] Wang et al., International Patent Application Publication No. WO2016/106348.

[35] Wang et al., International Patent Application Publication No. WO2016/118960.

[36] Wang et al., International Patent Application Publication No. WO2016/154136.

[37] Wang et al., International Patent Application Publication No. WO2016/197127.

[38] Wang et al., International Patent Application Publication No. WO2017/015381.

[39] Wang et al., International Patent Application Publication No. WO2017/019782.

[40] Wang et al., International Patent Application No. PCT/US2016/051755.

[41] Wang et al., International Patent Application NO. PCT/US2016/061890.

[42] Wang et al., International Patent Application NO. PCT/US2017/018456.

What is claimed is:

1. A system for performing X-ray computed tomography (CT) imaging, the system comprising:
an X-ray source;
a detector for detecting X-ray radiation from the X-ray source;
a filter grating disposed between the X-ray source and the detector to modify an X-ray energy spectrum of the X-ray radiation into two or more spectra, wherein the filter grating is positioned closer to the X-ray source than the detector is; and
an absorption grating aligned with the filter grating to selectively block at least a portion of the X-ray radiation,
wherein at least one of the absorption grating and the filter grating is configured to move relative to the other during operation of the X-ray source,
wherein the X-ray source is a kVp-switching X-ray source, and
wherein the absorption grating and the filter grating oscillate relative one another, and the oscillation is synchronized with a switching frequency of the X-ray source, such that each time the X-ray source switches its voltage level, at least one of the absorption grating and the filter grating moves relative to the other.

2. The system according claim 1, wherein an oscillation period of the relative movement between the gratings is equal to half a time interval between two adjacent X-ray projections of the X-ray source.

3. The system according to claim 1, wherein the X-ray source is a single-kVp X-ray source.

4. The system according to claim 3, wherein the relative movement of the gratings is an oscillation movement relative to each other that is optimized for the single-kVp X-ray source.

5. The system according to claim 1, wherein the filter grating comprises at least two different types of filter material.

6. The system according to claim 1, wherein the absorption grating comprises slit portions and solid portions disposed alternatingly.

7. The system according to claim 6, wherein a width of each slit portion of the absorption grating is the same as that of each other slit portion of the absorption grating.

8. The system according to claim 6, wherein a width of at least one slit portion of the absorption grating is narrower than that of each solid portion of the absorption grating.

9. The system according to claim 1, wherein the relative motion between the absorption grating and the filter grating is in a direction parallel to a front face of the absorption grating facing the X-ray source.

10. The system according to claim 1, wherein the filter grating comprises a plurality of strips of a first filter material, with a second filter material disposed alternatingly with the plurality of strips of the first filter material.

11. The system according to claim 1, wherein the filter grating moves while the absorption grating stays stationary during operation of the X-ray source.

* * * * *